(12) United States Patent
Den Boef et al.

(10) Patent No.: US 10,345,709 B2
(45) Date of Patent: Jul. 9, 2019

(54) DETERMINATION OF STACK DIFFERENCE AND CORRECTION USING STACK DIFFERENCE

(71) Applicant: ASML NETHERLANDS B.V., Veldhoven (NL)

(72) Inventors: Arie Jeffrey Den Boef, Waalre (NL); Kaustuve Bhattacharyya, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 16/127,296

(22) Filed: Sep. 11, 2018

(65) Prior Publication Data

US 2019/0025707 A1 Jan. 24, 2019

Related U.S. Application Data

(63) Continuation of application No. 15/474,803, filed on Mar. 30, 2017, now Pat. No. 10,078,268.

(30) Foreign Application Priority Data

Apr. 22, 2016 (EP) .................................... 16166614

(51) Int. Cl.
*G03F 7/20* (2006.01)
*G01N 21/47* (2006.01)
*G01N 21/956* (2006.01)

(52) U.S. Cl.
CPC ..... *G03F 7/70133* (2013.01); *G01N 21/4788* (2013.01); *G01N 21/956* (2013.01); *G03F 7/70625* (2013.01); *G03F 7/70633* (2013.01)

(58) Field of Classification Search
CPC ............. G03F 7/70633; G03F 7/70133; G03F 7/70483
(Continued)

(56) References Cited

U.S. PATENT DOCUMENTS

| | | | |
|---|---|---|---|
| 6,982,793 B1 | 1/2006 | Yang et al. | |
| 7,508,976 B1 | 3/2009 | Yang et al. | |

(Continued)

FOREIGN PATENT DOCUMENTS

| | | |
|---|---|---|
| WO | 2009/078708 | 6/2009 |
| WO | 2009/106279 | 9/2009 |

(Continued)

OTHER PUBLICATIONS

International Search Report and Written Opinion dated Jun. 29, 2017 in corresponding International Patent Application No. PCT/EP2017/057261.

(Continued)

*Primary Examiner* — Hung Nguyen
(74) *Attorney, Agent, or Firm* — Pillsbury Winthrop Shaw Pittman LLP

(57) ABSTRACT

A method including: obtaining a measurement of a metrology target on a substrate processed using a patterning process, the measurement having been obtained using measurement radiation; and deriving a parameter of interest of the patterning process from the measurement, wherein the parameter of interest is corrected by a stack difference parameter, the stack difference parameter representing an un-designed difference in physical configuration between adjacent periodic structures of the target or between the metrology target and another adjacent target on the substrate.

21 Claims, 14 Drawing Sheets

(58) Field of Classification Search
USPC .................................. 355/52, 53, 55, 77
See application file for complete search history.

(56) References Cited

U.S. PATENT DOCUMENTS

| | | | |
|---|---|---|---|
| 8,339,595 | B2 | 12/2012 | Den Boef |
| 8,411,287 | B2 | 4/2013 | Smilde et al. |
| 8,867,020 | B2 | 10/2014 | Smilde et al. |
| 9,081,303 | B2 | 7/2015 | Cramer et al. |
| 9,110,385 | B2 | 8/2015 | Den Boef |
| 9,134,256 | B2 | 9/2015 | Smilde et al. |
| 9,347,879 | B2 * | 5/2016 | Adel .................. G03F 7/70633 |
| 2010/0328655 | A1 | 12/2010 | Den Boef |
| 2011/0027704 | A1 | 2/2011 | Cramer et al. |
| 2011/0043791 | A1 | 2/2011 | Smilde et al. |
| 2011/0069292 | A1 | 3/2011 | Den Boef |
| 2012/0242970 | A1 | 9/2012 | Smilde et al. |
| 2013/0035888 | A1 | 2/2013 | Kandel et al. |
| 2013/0258310 | A1 | 10/2013 | Smilde et al. |
| 2013/0278942 | A1 | 10/2013 | Jeong et al. |
| 2015/0177166 | A1 | 6/2015 | Cramer et al. |
| 2016/0061589 | A1 | 3/2016 | Bhattacharyya |
| 2016/0313116 | A1 | 10/2016 | Ghinovker |
| 2016/0313654 | A1 | 10/2016 | Zeng et al. |

FOREIGN PATENT DOCUMENTS

| | | |
|---|---|---|
| WO | 2011/012624 | 2/2011 |
| WO | 2013/143814 | 10/2013 |
| WO | 2016/086056 | 6/2016 |

OTHER PUBLICATIONS

Turner, Kevin T. et al., "Monitoring process-induced overlay errors through high-resolution wafer geometry measurements", Proceedings of SPIE, vol. 9050, pp. 905013-1-905013-9 (2014).

* cited by examiner

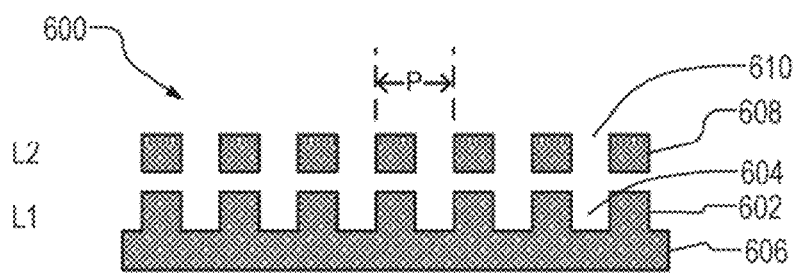
Fig. 7A
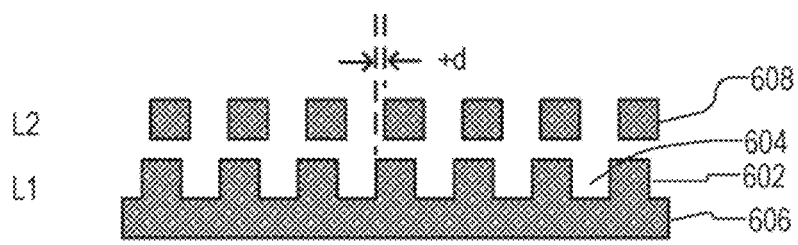
Fig. 7B
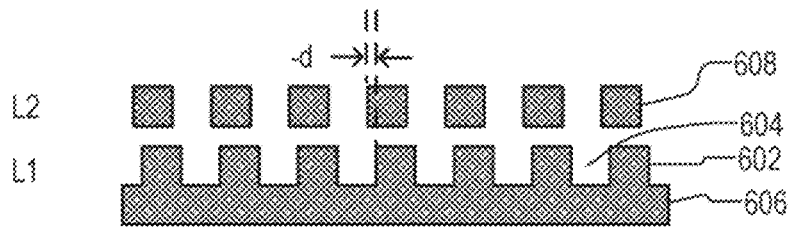
Fig. 7C
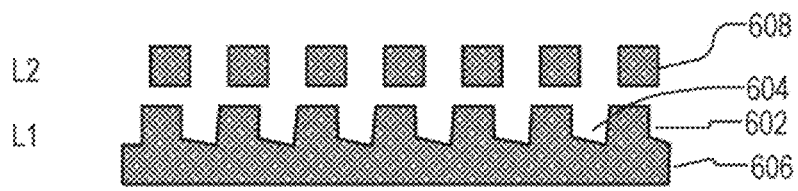
Fig. 7D

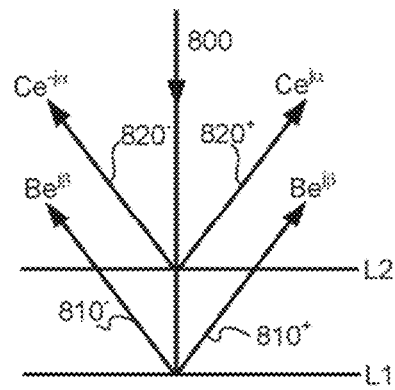 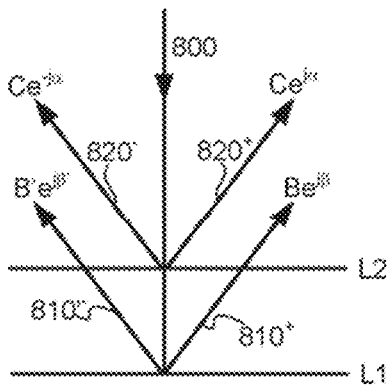
Fig. 10A        Fig. 10B
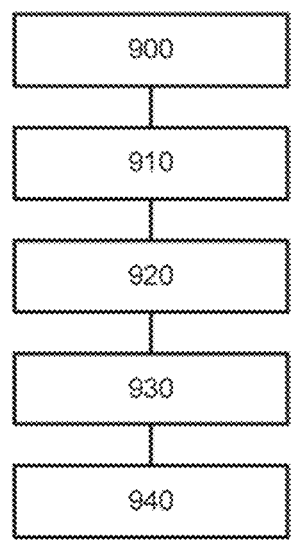
Fig. 11

DETERMINATION OF STACK DIFFERENCE AND CORRECTION USING STACK DIFFERENCE

This application is a continuation of U.S. patent application Ser. No. 15/474,803, which was filed on Mar. 30, 2017, now allowed, which claims the benefit of priority of European Patent Application No. 16166614.4, which was filed on Apr. 22, 2016. The entire content of each of the foregoing applications is incorporated herein by reference.

FIELD

The present disclosure relates to methods and apparatus for inspection (e.g., metrology) usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In a patterning process (i.e., a process of creating a device or other structure involving patterning (such as lithographic exposure or imprint), which may typically include one or more associated processing steps such as development of resist, etching, etc.), it is desirable to determine (e.g., measure, simulate using one or more models that model one or more aspects of the patterning process, etc.) one or more parameters of interest, such as the critical dimension (CD) of a structure, the overlay error between successive layers formed in or on the substrate, etc.

It is desirable to determine such one or more parameters of interest for structures created by a patterning process and use them for design, control and/or monitoring relating to the patterning process, e.g., for process design, control and/or verification. The determined one or more parameters of interest of patterned structures can be used for patterning process design, correction and/or verification, defect detection or classification, yield estimation and/or process control.

Thus, in patterning processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Various forms of inspection apparatus (e.g., metrology apparatus) have been developed for use in the lithographic field. These devices direct a beam of radiation onto a target and measure one or more properties of the redirected (e.g., scattered) radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

The targets used by inspection apparatus (e.g., a scatterometer) are relatively large, e.g., 40 µm by 40 µm, periodic structures (e.g., gratings) and the measurement beam generates a spot that is smaller than the periodic structure (i.e., the periodic structure is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the periodic structure is made smaller than the measurement spot (i.e., the periodic structure is overfilled). Typically such targets are measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated by reference in their entirety. Further developments of the technique have been described in U.S. patent application publication nos. US 2011-0027704, US 2011-0043791 and US 2012-0242970, each of which is incorporated herein in its entirety. Diffraction-based overlay using dark-field detection of the diffraction orders enables overlay measurements on smaller targets. These targets can be smaller than the illumination spot and may be surrounded by product structures on a substrate. A target can comprise multiple periodic structures, which can be measured in one image.

In a known metrology technique, overlay measurement results are obtained by measuring a target twice under certain conditions, while either rotating the target or changing the illumination mode or imaging mode to obtain separately the $-1^{st}$ and the $+1^{st}$ diffraction order intensities. The intensity asymmetry, a comparison of these diffraction order intensities, for a given target provides a measurement of target asymmetry, that is asymmetry in the target. This asymmetry in the target can be used as an indicator of overlay error (undesired misalignment of two layers).

SUMMARY

Although, in the example of overlay measurement, the overlay measurements are fast and computationally very simple (once calibrated), they rely on an assumption that overlay (i.e., overlay error and deliberate bias) is the only cause of target asymmetry in the target. Any other asymmetry in the target, such as structural asymmetry of features within the periodic structure in an upper layer, within the periodic structure in a lower layer overlaid by the periodic structure in the upper layer, or both, also causes an intensity asymmetry in the $1^{st}$ (or other higher) orders. This intensity asymmetry attributable to structural asymmetry, and which is not related to overlay, perturbs the overlay measurement, giving an inaccurate overlay measurement. Asymmetry in the lower or bottom periodic structure of a target is a common form of structural asymmetry. It may originate for example in substrate processing steps such as chemical-mechanical polishing (CMP), performed after the bottom periodic structure was originally formed.

It has been discovered that, in addition to or alternatively to structural asymmetry in a target, a stack difference between adjacent periodic structures of a target or between adjacent targets may be a factor that adversely affects the accuracy of measurement, such as overlay measurement. Stack difference may be understood as an un-designed difference in physical configurations between adjacent periodic structures or targets. Stack difference includes, but is not limited to, a thickness difference between the adjacent periodic structures or targets, a refractive index difference between the adjacent periodic structures or targets, a difference in material between the adjacent periodic structures or targets, a difference in the grating period of the structures of adjacent periodic structures or targets, etc. Like structural asymmetry, the stack difference may be introduced by processing steps, such as CMP, layer deposition, etc. in the patterning process.

Therefore, it is desired to distinguish the contributions to target asymmetry that are caused by overlay alone in a more direct and accurate way. It is also desirable to identify desired target designs, either separately or in combination with different measurement recipes.

In an embodiment, there is provided a method comprising: obtaining a measurement of a metrology target on a substrate processed using a patterning process, the measurement having been obtained using measurement radiation; and deriving a parameter of interest of the patterning process from the measurement, wherein the parameter of interest is corrected by a stack difference parameter, the stack difference parameter representing an un-designed difference in physical configuration between adjacent periodic structures of the target or between the metrology target and another adjacent target on the substrate.

In an embodiment, there is provided method comprising: obtaining first values of a stack difference parameter and second values of a stack difference parameter for a plurality of adjacent periodic structures of a measurement target or for a plurality of adjacent measurement targets, the first values of the stack difference parameter and second values of the stack difference parameter having been obtained with, respectively, measurements using first measurement radiation and second measurement radiation and the stack difference parameter representing an un-designed difference in physical configuration between adjacent periodic structures of a measurement target or between adjacent measurement targets on a substrate; obtaining first values of a target parameter and second values of the target parameter from the plurality of adjacent periodic structures of the measurement target or for the plurality of adjacent measurement targets, the first values of the target parameter and second values of the target parameter having been obtained with, respectively, the first measurement radiation and the second measurement radiation and wherein the target parameter value comprises a part which is independent of the un-designed difference in physical configuration, and a part due to the un-designed difference in physical configuration; determining a relationship function describing the relationship between the first and/or second values of stack difference parameter and the difference of the first values of the target parameter and the second values of the target parameter; and determining a part of a target parameter value which is independent of the un-designed difference in physical configuration from the relationship function.

In an embodiment, there is provided a method of selecting a target from a plurality of candidate targets, the method comprising: obtaining plural sets of values for a plurality of candidate measurement radiation pairs and a plurality of candidate targets, each candidate target comprising a first periodic structure horizontally adjacent to a second periodic structure, each set of values relating to a different combination of one of the candidate targets and one of the candidate measurement radiation pairs, each set of values comprising, for multiple samples of the candidate target: first values of stack difference parameter and second values of stack difference parameter of the adjacent periodic structures of the candidate target using, respectively, a first measurement radiation and a second measurement radiation of the candidate measurement radiation pair, the stack difference parameter representing an un-designed difference in physical configuration between adjacent periodic structures of a target; first values of target parameter and second values of target parameter of the candidate target using, respectively, the first measurement radiation and the second measurement radiation; for each set of values, determining a degree of correlation between the first and/or second values of stack difference parameter and the difference of the first values of target parameter and the second values of target parameter; and selecting a desired target from one of the candidate targets based upon the determined degree of correlation for each set of values.

Further features and advantages, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments will now be described, by way of example only, with reference to the accompanying drawings in which:

FIG. 7A, FIG. 7B and FIG. 7C respectively show schematic cross-sections of overlay periodic structures having different overlay values in the region of zero;

FIG. 7D is a schematic cross-section of an overlay periodic structure having structural asymmetry in a bottom periodic structure due to processing effects;

FIG. 10A illustrates diffraction signals following diffraction by a target comprising first and second overlaid periodic structures with no structural asymmetry in the first layer;

FIG. 10B illustrates diffraction signals following diffraction by a target comprising first and second overlaid structures with structural asymmetry in the first layer;

FIG. 11 is a flowchart of steps of a method according to an embodiment;

DETAILED DESCRIPTION

Before describing embodiments in detail, it is instructive to present an example environment in which embodiments may be implemented.

Figure 1:
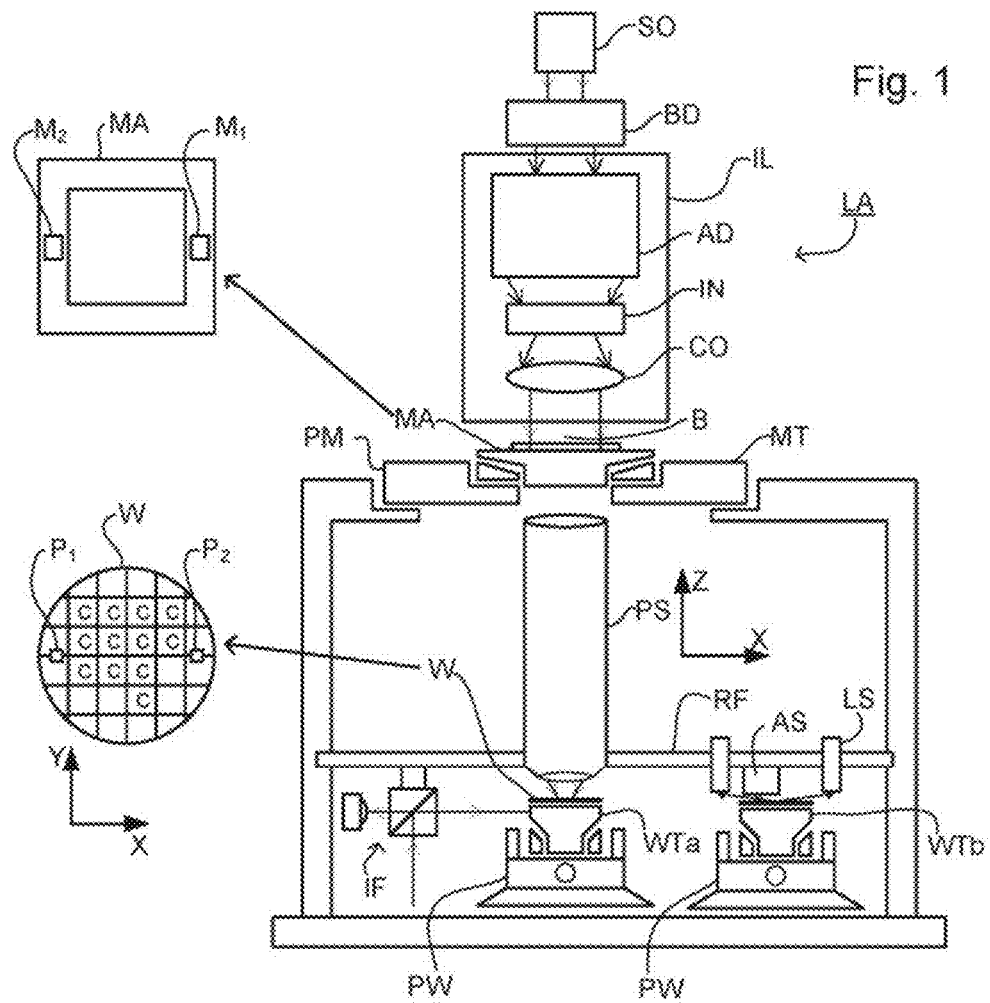
FIG. 1 depicts an embodiment of a lithographic apparatus.

FIG. 1 schematically depicts a lithographic apparatus LA. The apparatus includes an illumination optical system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection optical system (e.g., a refractive projection lens system) PS configured to project a pattern imparted to the radiation beam B by patterning device MA onto a target portion C (e.g., including one or more dies) of the substrate W.

The illumination optical system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table) MT, and is patterned by the patterning device. Having traversed the patterning device (e.g., mask) MA, the radiation beam B passes through the projection optical system PS, which focuses the beam onto a target portion C of the substrate W, thereby projecting an image of the pattern on the target portion C. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using patterning device alignment marks $M_1$, $M_2$ and substrate alignment marks $P_1$, $P_2$. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the patterning device alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

Lithographic apparatus LA in this example is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus.

The depicted apparatus can be used in a variety of modes, including for example a step mode or a scan mode. The construction and operation of lithographic apparatus is well known to those skilled in the art and need not be described further for an understanding of the embodiments of the present invention.

Figure 2:
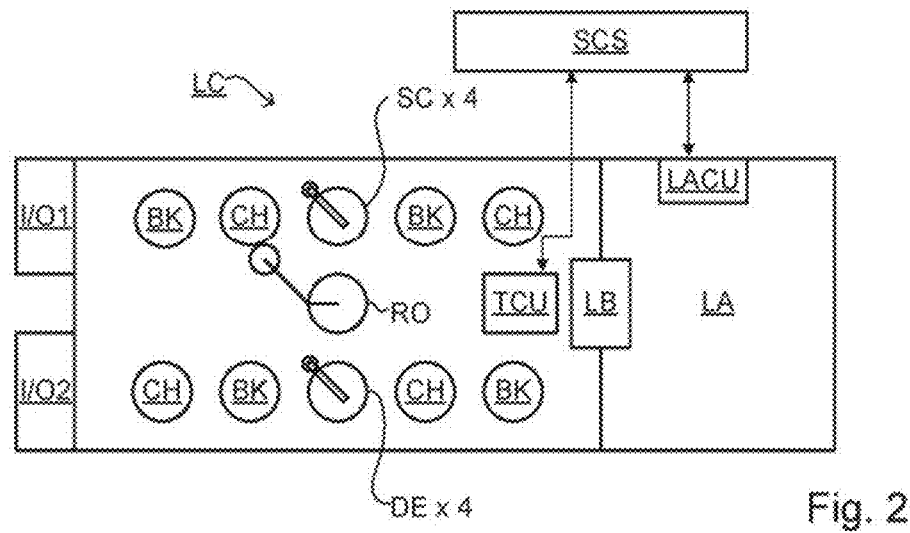
FIG. 2 depicts an embodiment of a lithographic cell or cluster.

As shown in FIG. 2, the lithographic apparatus LA forms part of a lithographic system, referred to as a lithographic cell LC or a lithocell or cluster. The lithographic cell LC may also include apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Figures 3A, 3B, 3C, 3D, 4, 5:
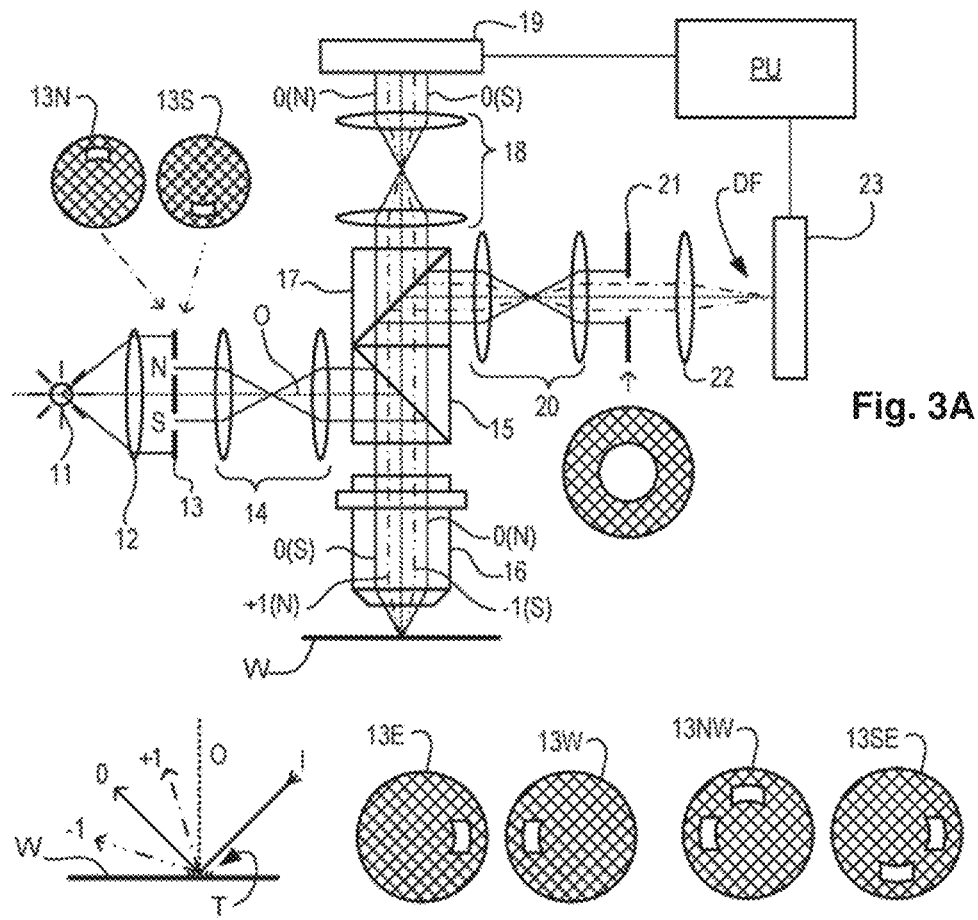
FIG. 3A depicts a schematic diagram of an inspection apparatus (e.g., a dark field scatterometer in this case) configured to measure a target using a first pair of illumination apertures.
FIG. 3B schematically depicts a detail of a diffraction spectrum of a target periodic structure for a given direction of illumination.
FIG. 3C schematically depicts a second pair of illumination apertures providing further illumination modes in using the inspection apparatus of FIG. 3A for diffraction based overlay measurements.
FIG. 3D schematically depicts a third pair of illumination apertures combining the first and second pair of apertures.
FIG. 4 depicts a form of multiple periodic structure target and an outline of a measurement spot on a substrate.
FIG. 5 depicts an image of the target of FIG. 4 obtained in the inspection apparatus of FIG. 3.

An inspection apparatus suitable for use in embodiments is shown in FIG. 3A. A target T and diffracted rays of measurement radiation used to illuminate the target are illustrated in more detail in FIG. 3B. The inspection apparatus illustrated is of a type known as a dark field metrology apparatus. The inspection apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by source 11 (e.g., a xenon lamp) is directed onto substrate W via optical element 15 by an optical system comprising lenses 12, 14 and objective lens 16. These lenses are arranged in a double sequence of a 4F arrangement. A different lens arrangement can be used, provided that it, e.g., provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis radiation from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode will interfere with the desired measurement signals.

As shown in FIG. 3B, target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitches of the targets and the illumination angles can be designed or adjusted so that the first order rays entering the objective lens are closely aligned with the central optical axis. The rays illustrated in FIGS. 3A and 3B are shown somewhat off axis, purely to enable them to be more easily distinguished in the diagram.

At least the 0 and $+1^{st}$ orders diffracted by the target T on substrate W are collected by objective lens 16 and directed back through optical element 15. Returning to FIG. 3A, both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the inspection apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the periodic structure features as such will not be formed, if only one of the $−1^{st}$ and $+1^{st}$ orders is present.

The particular forms of aperture plate 13 and field stop 21 shown in FIGS. 3A, 3C and 3D are purely examples. In an embodiment, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 3A, 3B, 3C or 3D) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure periodic structures oriented in one direction (X or Y depending on the set-up). For measurement of an orthogonal periodic structure, rotation of the target through 90° and 270° might be implemented. Different aperture plates are shown in FIGS. 3C and 3D. The use of these, and numerous other variations and applications of the apparatus are described in the patent application publications mentioned above.

FIG. 4 depicts a (composite) target formed on a substrate according to known practice. The target in this example comprises four periodic structures (e.g., gratings) 32 to 35 positioned closely together so that they will all be within a measurement spot 31 formed by the metrology radiation illumination beam of the inspection apparatus. The four periodic structures thus are all simultaneously illuminated and simultaneously imaged on sensors 19 and 23. In an example dedicated to measurement of overlay, periodic structures 32 to 35 are themselves composite periodic structures formed by overlying periodic structures that are patterned in different layers of, e.g., the semi-conductor device formed on substrate W. Periodic structures 32 to 35 may have differently biased overlay offsets in order to facilitate measurement of overlay between the layers in which the different parts of the composite periodic structures are formed. The meaning of overlay bias will be explained below with reference to FIG. 7. Periodic structures 32 to 35 may also differ in their orientation, as shown, so as to diffract incoming radiation in X and Y directions. In one example, periodic structures 32 and 34 are X-direction periodic structures with bias offsets of +d, −d, respectively. Periodic structures 33 and 35 are Y-direction periodic structures with bias offsets +d, −d respectively. Separate images of these periodic structures can be identified in the image captured by sensor 23. This is only one example of a target. A target may comprise more or fewer than 4 periodic structures, or only a single periodic structure.

FIG. 5 shows an example of an image that may be formed on and detected by the sensor 23, using the target of FIG. 4 in the apparatus of FIG. 3, using the aperture plates 13NW or 13SE from FIG. 3D. While the pupil plane image sensor 19 cannot resolve the different individual periodic structures 32 to 35, the image sensor 23 can do so. The dark rectangle represents the field of the image on the sensor, within which the illuminated spot 31 on the substrate is imaged into a corresponding circular area 41. Within this, rectangular areas 42-45 represent the images of the small target periodic structures 32 to 35. If the targets are located in product areas, product features may also be visible in the periphery of this image field. Image processor and control system PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the patterning process. Overlay performance is an important example of such a parameter.

Figure 6:
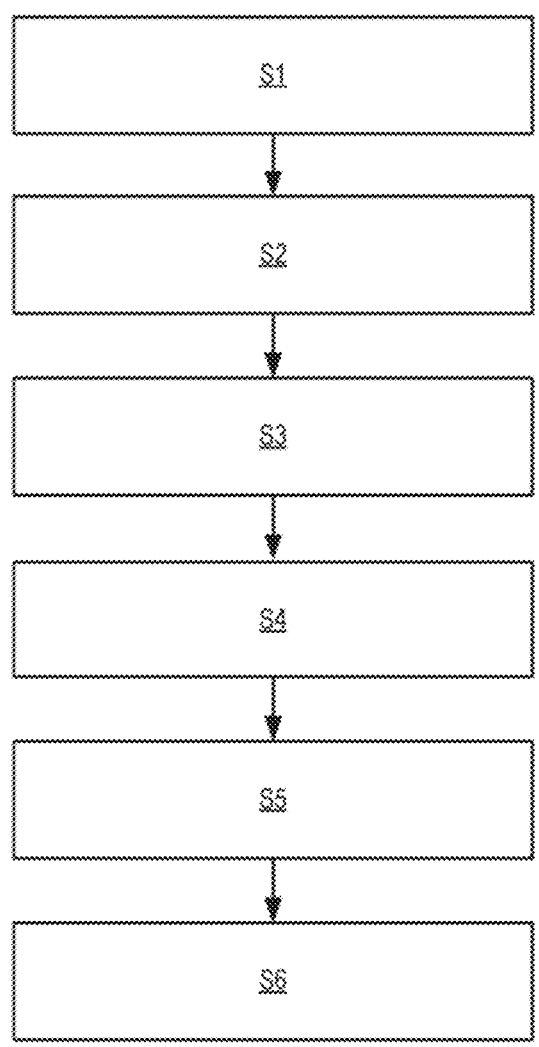
FIG. 6 is a flowchart showing steps of an overlay measurement method using the inspection apparatus of FIG. 3.

FIG. 6 illustrates how, using for example the method described in PCT patent application publication no. WO 2011/012624, overlay error (i.e., undesired and unintentional overlay misalignment) between the two layers containing the component periodic structures 32 to 35 is measured. This measurement is done through identifying target asymmetry, as revealed by comparing the intensities in the $+1^{st}$ order and $-1^{st}$ order dark field images of the target periodic structures (the intensities of other corresponding higher orders can be compared, e.g. $+2^{nd}$ and $-2^{nd}$ orders) to obtain a measure of the intensity asymmetry. At step S1, the substrate, for example a semiconductor wafer, is processed through a lithographic apparatus, such as the lithographic cell of FIG. 2, one or more times, to create a target including the periodic structures 32-35. At S2, using the inspection apparatus of FIG. 3, an image of the periodic structures 32 to 35 is obtained using only one of the first order diffracted beams (say −1). At step S3, whether by changing the illumination mode, or changing the imaging mode, or by rotating substrate W by 180° in the field of view of the inspection apparatus, a second image of the periodic structures using the other first order diffracted beam (+1) can be obtained. Consequently the +1 diffracted radiation is captured in the second image.

Note that, by including only half of the first order diffracted radiation in each image, the 'images' referred to here are not conventional dark field microscopy images. The individual target features of the target periodic structures will not be resolved. Each target periodic structure will be represented simply by an area of a certain intensity level. In step S4, a region of interest (ROI) is identified within the image of each component target periodic structure, from which intensity levels will be measured.

Having identified the ROI for each individual target periodic structure and measured its intensity, the asymmetry of the target, and hence overlay error, can then be determined. This is done (e.g., by the processor PU) in step S5 comparing the intensity values obtained for $+1^{st}$ and $-1^{st}$ orders for each target periodic structure 32-35 to identify their intensity asymmetry, e.g., any difference in their intensity. The term "difference" is not intended to refer only to subtraction. Differences may be calculated in ratio form. In step S6 the measured intensity asymmetries for a number of target periodic structures are used, together with knowledge of any known imposed overlay biases of those target periodic structures, to calculate one or more performance parameters of the patterning process in the vicinity of the target T.

In applications described herein, measurements using two or more different measurement recipes will be included. A performance parameter of great interest is overlay. As will be described later, other parameters of performance of the patterning process can be calculated. The performance parameter (e.g., overlay, CD, focus, dose, etc.) can be fed back (or fed forward) for improvement of the patterning process, improvement of the target, and/or used to improve the measurement and calculation process of FIG. 6 itself.

In the patent application publications mentioned above, various techniques are disclosed for improving the quality of overlay measurements using the basic method mentioned above. These techniques will not be explained here in further detail. They may be used in combination with the techniques newly disclosed in the present application.

FIG. 7 shows schematic cross sections of target periodic structures (overlay periodic structures), with different bias offsets. These can be used as the target T on substrate W, as seen in FIGS. 3 and 4. Periodic structures with periodicity in the X direction are shown for the sake of example only. Different combinations of these periodic structures with different biases and with different orientations can be provided separately or as part of a target.

Starting with FIG. 7A, a target 600 formed in at least two layers, labeled L1 and L2, is shown. In the lower or bottom layer L1, a first periodic structure (the lower or bottom periodic structure), for example a grating, is formed by features 602 and spaces 604 on a substrate 606. In layer L2, a second periodic structure, for example a grating, is formed by features 608 and spaces 610. (The cross-section is drawn such that the features 602, 608 (e.g., lines) extend into the page.) The periodic structure pattern repeats with a pitch P in both layers. Features 602 and 608 may take the form of lines, dots, blocks and via holes. In the situation shown at FIG. 7A, there is no overlay contribution due to misalignment, e.g., no overlay error and no imposed bias, so that each feature 608 of the second structure lies exactly over a feature 602 in the first structure.

At FIG. 7B, the same target with a first known imposed bias +d is shown, such that the features 608 of the first structure are shifted by a distance d to the right, relative to the features of the second structure. The bias distance d might be a few nanometers in practice, for example 10 nm-20 nm, while the pitch P is for example in the range 300-1000 nm, for example 500 nm or 600 nm. At FIG. 7C, another feature with a second known imposed bias −d, such that the features of 608 are shifted to the left, is depicted. The value of d need not be the same for each structure. Biased periodic structures of this type shown at FIGS. 7A to 7C are described in the prior patent application publications mentioned above.

FIG. 7D shows schematically a phenomenon of structural asymmetry, in this case structural asymmetry in the first structure (bottom structure asymmetry). The features in the periodic structures at FIGS. 7A to 7C, are shown as perfectly square-sided, when a real feature would have some slope on the side, and a certain roughness. Nevertheless they are intended to be at least symmetrical in profile. The features 602 and/or spaces 604 at FIG. 7D in the first structure no longer have a symmetrical form at all, but rather have become distorted by one or more processing steps. Thus, for example, a bottom surface of each space has become tilted (bottom wall tilt). For example, side wall angles of the features and spaces have become asymmetrical. As a result of this, the overall target asymmetry of a target will comprise an overlay contribution independent of structural asymmetry (i.e., an overlay contribution due to misalignment of the first structure and second structure; itself comprised of overlay error and any known imposed bias) and a structural contribution due to this structural asymmetry in the target.

When overlay is measured by the method of FIG. 6 using only two biased periodic structures, the process-induced structural asymmetry cannot be distinguished from the overlay contribution due to misalignment, and overlay measurements (in particular to measure the undesired overlay error) become unreliable as a result. Structural asymmetry in the first structure (bottom periodic structure) of a target is a common form of structural asymmetry. It may originate, for example, in the substrate processing steps such as chemical-mechanical polishing (CMP), performed after the first structure was originally formed.

In PCT patent application publication no. WO 2013-143814, it is proposed to use three or more component periodic structures to measure overlay by a modified version of the method of FIG. 6. Three or more periodic structures of the type shown in FIGS. 7A to 7C are used to obtain overlay measurements that are to some extent corrected for structural asymmetry in the target periodic structures, such as is caused by bottom structure asymmetry in a practical patterning process. However, this method requires a new target design (e.g. different to that illustrated in FIG. 4) and therefore a new patterning device or patterning device pattern will be required. Furthermore, the target area is larger and therefore consumes more substrate area. In addition, the phase element of the overlay contribution resultant from structural asymmetry is ignored in this and other prior methods, meaning that the corrections are not as accurate as they could be if the phase element was also corrected for.

Figure 8:
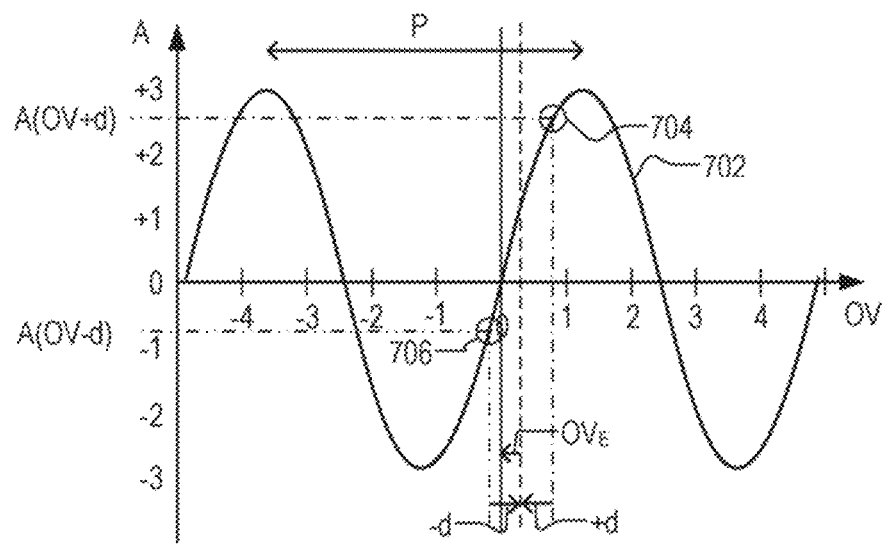
FIG. 8 illustrates principles of overlay measurement in an ideal target, not subject to structural asymmetry.
Figure 9:
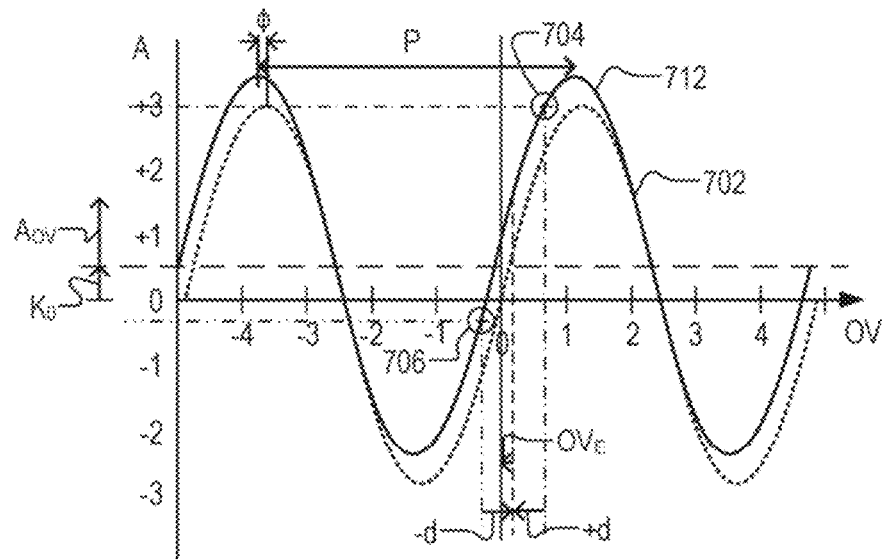
FIG. 9 illustrates principles of overlay measurement in a non-ideal target, with correction of structural asymmetry as disclosed in embodiments herein.

In FIG. 8 a curve 702 illustrates the relationship between overlay OV and intensity asymmetry A for an 'ideal' target having zero offset and no structural asymmetry within the individual periodic structures forming the target, and in particular within the individual periodic structure of the first structure. Consequently, the target asymmetry of this ideal target comprises only an overlay contribution due to misalignment of the first structure and second structure resultant from a known imposed bias and overlay error $OV_E$. This graph, and the graph of FIG. 9, illustrate the principles behind the disclosure only, and in each graph, the units of intensity asymmetry A and overlay OV are arbitrary. Examples of actual dimensions will be given further below.

In the 'ideal' situation of FIG. 8, the curve 702 indicates that the intensity asymmetry A has a non-linear periodic relationship (e.g., sinusoidal relationship) with the overlay. The period P of the sinusoidal variation corresponds to the period or pitch P of the periodic structures, converted of course to an appropriate scale. The sinusoidal form is pure in this example, but can include harmonics in real circumstances.

As mentioned above, biased periodic structures (having a known imposed overlay bias) can be used to measure overlay, rather than relying on a single measurement. This bias has a known value defined in the patterning device (e.g. a reticle) from which it was made, that serves as an on-substrate calibration of the overlay corresponding to the measured intensity asymmetry. In the drawing, the calculation is illustrated graphically. In steps S1-S5, intensity asymmetry measurements A+d and A−d are obtained for periodic structures having imposed biases +d and −d respectively (as shown in FIG. 7B and FIG. 7C, for example). Fitting these measurements to the sinusoidal curve gives points 704 and 706 as shown. Knowing the biases, the true overlay error $OV_E$ can be calculated. The pitch P of the sinusoidal curve is known from the design of the target. The vertical scale of the curve 702 is not known to start with, but is an unknown factor which can be referred to as a 1st harmonic proportionality constant, $K_1$. This constant $K_1$ is a measure of the sensitivity of the intensity asymmetry measurements to the target.

In equation terms, the relationship between overlay error $OV_E$ and intensity asymmetry A is assumed to be:

$$A_{\pm d} = K_1 \sin(OV_E \pm d) \tag{1}$$

where overlay error $OV_E$ is expressed on a scale such that the target pitch P corresponds to an angle $2\pi$ radians. Using two measurements of gratings with different, known biases (e.g. +d and −d), the overlay error $OV_E$ can be calculated using:

$$OV_E = a\tan\left(\frac{A_{+d} + A_{-d}}{A_{+d} - A_{-d}} \cdot \tan(d)\right) \tag{2}$$

FIG. 9 shows a first effect of introducing structural asymmetry, for example the bottom periodic structure asymmetry illustrated in FIG. 7D. The 'ideal' sinusoidal curve 702 no longer applies. However, at least approximately, bottom periodic structure asymmetry or other structural asymmetry has the effect of adding an intensity shift term $K_0$ and a phase shift term $\phi$ to the intensity asymmetry $A_{\pm d}$. The resulting curve is shown as 712 in the diagram, with label $K_0$ indicating the intensity shift term, and label $\phi$ indicating the phase offset term. The intensity shift term $K_0$ and phase shift term $\phi$ are dependent upon a combination of the target and a selected characteristic of the measurement radiation, such as the wavelength and/or polarization of the measurement radiation (the "measurement recipe"), and is sensitive to process variations. In equation terms, the relationship used for calculation in step S6 becomes:

$$A_{\pm d} = K_0 + K_1 \sin(OV_E \pm d + \phi) \tag{3}$$

Where there is structural asymmetry, the overlay model described by equation (2) will provide overlay error values which are impacted by the intensity shift term $K_0$ and phase shift term $\phi$, and will be inaccurate as a consequence. The structural asymmetry will also result in differences in measurements of the same target using different measurement recipes, when mapping the overlay error, because intensity and phase shift are wavelength and/or polarization dependent. Thus, it would be desirable to optimize selection of the target-measurement recipe combination so as to obtain more accurate overlay error measurements, or to remove the overlay contribution due to structural asymmetry, thereby correcting the overlay error measurements. Therefore, slight changes in substrate processing, or changes in the measurement recipe will lead to overlay variation, thereby impacting the overlay control loop APC (Automatic Process Control) and the device yield.

The overlay calculations of modified step S6 rely on certain assumptions. Firstly, it is assumed intensity asymmetry behaves as a sine function of the overlay, with the period P corresponding to the grating pitch. These assumptions are valid for present overlay ranges. The number of harmonics can be designed to be small, because the small pitch-wavelength ratio only allows for a small number of propagating diffraction orders from the grating. However, in practice the overlay contribution to the intensity asymmetry due to misalignment may not necessarily be truly sinusoidal, and may not necessarily be completely symmetrical about OV=0.

It is proposed to measure the target asymmetry of a target, and therefore overlay which does not neglect the effect of the structural asymmetry, while allowing the use of current target designs such as those illustrated in FIG. 4. This modelling may be performed as a modification to step S6 in the method illustrated in FIG. 6. The method proposed can calculate overlay errors accurately using real substrate measurement data, and which can determine the optimal or desired combination of targets and measurement recipes. No simulation or reconstruction may be needed.

In particular, it has been observed that, for the overlay range of interest, both the intensity term and phase term of the overlay contribution due to structural asymmetry is independent of the overlay contribution due to misalignment.

FIG. 10A shows an incident measurement radiation beam 800 onto a target comprising a first structure L1 and second structure L2 for the case where the second structure comprises no structural asymmetry. The resultant $+1^{st}$ diffraction order 810$^+$ from the first structure has an intensity $Be^{j\beta}$ and the $+1^{st}$ diffraction order 820$^+$ from the second structure has an intensity $Ce^{j\alpha}$. These intensities combine to produce an intensity $I_{+1}$ for the $+1^{st}$ diffraction order of the target:

$$I_{+1} = |Ce^{j\alpha} + Be^{j\beta}|^2 = B^2 + C^2 + 2BC \times \cos[\beta + \alpha] \quad (4)$$

where B and C are intensity scaling factors, $$\alpha = 2\pi \frac{OV}{P}, \quad \beta = 4\pi \frac{T}{\lambda},$$

OV is the overlay, P is the target pitch, T is the target thickness, and $\lambda$ is the measurement radiation wavelength.

Similarly, the resultant $-1^{st}$ diffraction order 810$^-$ from the first structure has an intensity $Be^{j\beta}$ and the $-1^{st}$ diffraction order 820$^-$ from the second structure has an intensity $Ce^{-j\alpha}$. These intensities combine to produce an intensity $I_{-1}$ for the $-1^{st}$ diffraction order of the target:

$$I_{-1} = |Ce^{-j\alpha} + Be^{j\beta}|^2 = B^2 + C^2 + 2BC \times \cos[\beta - \alpha] \quad (5)$$

FIG. 10B shows an incident radiation beam 800 onto a target comprising a first structure L1 and second structure L2 for the case where the first structure comprises structural asymmetry (structural asymmetry tends to be found in the bottom structure). Because of the structural asymmetry in the first structure, the $+1^{st}$ and $-1^{st}$ diffraction orders from the first structure are not the same. In the specific example shown here the $+1^{st}$ diffraction order 810$^+$ from the first structure has an intensity $Be^{j\beta}$, while the $-1^{st}$ diffraction order 810$^-$ from the first structure has an intensity $B'e^{j\beta'}$, where B' is different to B and $\beta'$ is different to $\beta$. Consequently, in this example, the intensities combine to produce an intensity $I^{-1}$ for the $-1^{st}$ diffraction order of the target (intensity $I^{+1}$ is the same as equation (4)):

$$I_{-1} = |Ce^{-j\alpha} + B'e^{j\beta'}|^2 = B^2 + C^2 + 2B'C \times \cos[\beta' - \alpha] \quad (6)$$

Derived from equations (4) and (6), when performing overlay measurements using targets with known imposed biases +d and −d, the intensity asymmetry can be formulated in terms of a phase term and an intensity term (the + and − subscript denotes the order of the measurement radiation beam and the +d and −d superscript denotes the target bias):

$$A^{+d} = I_{+1}^{+d} - I_{-1}^{+d} = 2BC \times \cos(\alpha + \varepsilon + \beta) - 2B'C \times \cos(\alpha + \varepsilon - \beta') + B^2 - B'^2 \quad (7)$$

$$A^{-d} = I_{+1}^{-d} - I_{-1}^{-d} = 2BC \times \cos(\alpha - \varepsilon + \beta) - 2B'C \times \cos(\alpha - \varepsilon - \beta') + B^2 - B'^2 \quad (8)$$

where:

$$\alpha^{+d} = 2\pi \frac{OV_E + d}{P} = \alpha + \varepsilon, \quad \alpha^{-d} = 2\pi \frac{OV_E - d}{P} = \alpha - \varepsilon, \quad \alpha = 2\pi \frac{OV_E}{P},$$

$$\varepsilon = 2\pi \frac{d}{P}, \quad \beta = 4\pi \frac{T}{\lambda}, \quad \frac{OV_E}{P} \ll 1 \Rightarrow \sin(\alpha) \approx \alpha \text{ and } \cos(\alpha) \approx 1$$

In each of equation (7) and equation (8), the "intensity term" of the asymmetry signal $A^{\pm d}$ (the terms which impact the intensity shift term) comprises the last two terms ($B^2 - B'^2$) of the equation. The "phase term" of the asymmetry signal $A^{\pm d}$ (the terms which impact the phase shift term) comprises the remaining terms of these equations. By applying these equations into the equation for the overlay contribution due to structural asymmetry $OV_{SA}$, the following is obtained:

$$OV_{SA} = \quad (9)$$

$$d \times \frac{A^{+d} + A^{-d}}{A^{+d} - A^{-d}} - OV_E = \left\{ \left( \frac{B \times \cos(\alpha + \beta) - B' \times \cos(\alpha + \beta')}{-B \times \sin(\alpha + \beta) - B' \times \sin(\alpha + \beta')} - \alpha \right) + \left( \frac{2(B^2 - B'^2)}{-4BC \times \sin(\alpha + \beta) + 4B'C \times \sin(\alpha - \beta')} \right) \right\} \times \frac{p}{2\pi}$$

assuming $\cos(d) \approx 1$, $\sin(d) \approx d$

The second term is the intensity term of the overlay contribution due to structural asymmetry $OV_{SA}$ and the remainder is the phase term of the overlay contribution due to structural asymmetry $OV_{SA}$.

Provided that $\beta \neq 0$ and $\beta' \neq 0$ (or are not close to 0), and the overlay range is small (e.g., within +/−20 nm) such that a is very small and $\sin \alpha \approx \alpha$, then:

$$OV_{SA} \approx \frac{B \times \cos(\beta) - B' \times \cos(\beta')}{-B \times \sin(\beta) + B' \times \sin(\beta')} \times \frac{p}{2\pi} + k \times 2(B^2 - B'^2) \quad (10)$$

Once again the second term is the intensity term and the remainder is the phase term. k is a constant.

The assumptions made to obtain equation (10) are valid for most cases. If $\beta \approx 0$ or $\beta' \approx 0$, the stack sensitivity would be very small and the measurement recipe would be filtered out during recipe optimization. Also, the overlay range would not be expected to exceed +/−20 nm. Therefore, in most cases, the overlay contribution due to structural asymmetry $OV_{SA}$ is constant and independent of overlay. As such, plots of overlay with and without the overlay contribution due to structural asymmetry would comprise essentially parallel lines within an overlay range of small overlay. This can be seen in FIG. 9, around OV=0.

The total overlay OV (i.e., the measured overlay) can be represented in terms of the overlay contribution due to structural asymmetry $OV_{SA}$ and an overlay contribution independent of structural asymmetry $OV_{NSA}$:

$$OV = OV_{NSA} + OV_{SA} \quad (11)$$

The overlay contribution independent of structural asymmetry $OV_{NSA}$ may comprise the overlay error $OV_E$ (any unintentional misalignment of the layers) and/or any known imposed bias d. Separating the overlay contribution due to structural asymmetry $OV_{SA}$ into constituent intensity term $OV_{SAI}$ and phase term $OV_{SA\phi}$ yields:

$$OV = OV_{NSA} + (OV_{SAI} + OV_{SA\phi}) \quad (12)$$

As can be derived from equation (10), constituent intensity term $OV_{SAI}$ of the overlay contribution due to structural asymmetry is proportional to the structural asymmetry in the lower grating BGA (where γ is a proportionality constant):

$$OV_{SAI} = \gamma * BGA \quad (13)$$

Assuming that there is a relationship G (which can be referred to as the process robustness index) between intensity term $OV_{SAI}$ and phase term $OV_{SA\phi}$:

$$OV_{SA\phi} = G * OV_{SAI} \quad (14)$$

Equation (12) can therefore be rewritten:

$$\begin{aligned} OV &= OV_{NSA} + \gamma * BGA + G * OV_{SAI} \\ &= OV_{NSA} + \gamma * BGA + G * \gamma * BGA \\ &= OV_{NSA} + \xi_{BGA} * BGA \end{aligned} \quad (15)$$

where $\xi_{BGA} = \gamma + G * \gamma$. Provided that the relationship function $\xi_{BGA}$ is constant across the substrate then, by determining relationship function $\xi_{BGA}$, it is possible to determine the overlay which is independent of structural asymmetry $OV_{NSA}$. This overlay measurement therefore does not include the overlay contribution due to structural asymmetry $OV_{SA}$, which combines the intensity term and phase term. A constant relationship function $\xi$ also indicates that the process robustness index G is also constant across the substrate, even with stack variation. So a constant relationship function $\xi$ indicates that the measurement recipe is robust to process variation.

The relationship function $\xi_{BGA}$ can be found by measuring the targets on a substrate using two different measurement recipes. In this case:

$$OV_A = OV_{NSA,A} + \xi_{BGA,A} * BGA_A$$

$$OV_B = OV_{NSA,B} + \xi_{BGA,B} * BGA_B$$

$$\Delta OV = \xi_{BGA,A} * BGA_A - \xi_{BGA,B} * BGA_B + C \quad (16)$$

where the subscripts A and B denote terms attributable to measurements made using measurement recipe A (a first measurement recipe) and measurement recipe B (a second measurement recipe) respectively; with $OV_A$ and $OV_B$ being the measured overlay with measurement recipe A and measurement recipe B respectively. $\Delta OV$ is the difference between the measured overlay $OV_A$ using measurement recipe A and the measured overlay $OV_B$ using measurement recipe B. Equation (16) is further based upon the assumption that $OV_{NSA,A} = OV_{NSA,B} = OV_{NSA}$. In other words, the overlay which is independent of structural asymmetry is assumed to be independent of the measurement recipe. It is only the structural asymmetry signal BGA which is dependent on measurement recipe.

Measurement recipe A and B can differ in wavelength and/or polarization of the measurement radiation.

In one embodiment, the relationship function $\xi_{BGA}$ can be found by determining the relationship between the measured structural asymmetry in lower grating $BGA_A$ using measurement recipe A, the measured structural asymmetry in lower grating $BGA_B$ using measurement recipe B and the difference in overlay measurements $\Delta OV$ between measurement recipes A and B. The validity of assuming (e.g. fitting) a constant relationship function when the measurements of all targets show a linear/planar correlation is described below.

FIG. 11 is a flowchart of a method of determining a relationship function and determining a patterning process parameter (e.g., overlay) according to an exemplary embodiment. The method is performed on a substrate comprising a number of targets. The steps of the method are as follows, and are then described in greater detail thereafter:

900—Measure $BGA_A$ and $BGA_B$ on targets with recipe A and recipe B, respectively;

910—Measure $OV_A$ and $OV_B$ on targets with recipe A and recipe B, respectively;

920—Plot $BGA_A$, $BGA_B$ and $\Delta OV$ as a 3D plot;

921 930—Find relationship functions $\xi_{BGA,A}$ and $\xi_{BGA,B}$; and

940—Find the corrected overlay.

At step 900, the structural asymmetry $BGA_A$ in the first structures of each target (or subsets thereof) is measured using a first measurement recipe A thereby obtaining a first measurement of structural asymmetry in the first structures. Also, the structural asymmetry $BGA_B$ in the first structures of each target (or subsets thereof) is measured using a second measurement recipe B thereby obtaining a second measurement of structural asymmetry in the first structures.

The first and second measurements of structural asymmetry may be performed before exposure of the second structures which, together with the first structures, make up the targets. In an embodiment, a measurement of structural asymmetry and a measurement of overlay can be obtained by a single measurement. This can be achieved by measuring together two neighboring structures, one comprising a first structure only (before a second structure has been exposed over it) and the other comprising a complete target (comprising a first structure overlaid with a second structure).

At step 910, the overlay $OV_A$ of each target (or subsets thereof) is measured using the first measurement recipe A, thereby obtaining a first measurement of target asymmetry in the targets. Also, the overlay $OV_B$ of each target (or subsets thereof) is measured using the second measurement recipe B, thereby obtaining a second measurement of target asymmetry in the targets.

At step 920, a 3D plot may be constructed, plotting $\Delta OV$ (the difference of measured overlay $OV_A$ and measured overlay $OV_B$) against the first measurement of structural asymmetry in the first structures $BGA_A$, on one axis and the second measurement of structural asymmetry in the first structures $BGA_B$ on another axis. In an embodiment, an actual plot need not be made but rather the data can be analyzed in such a 3D fashion.

Figure 12:
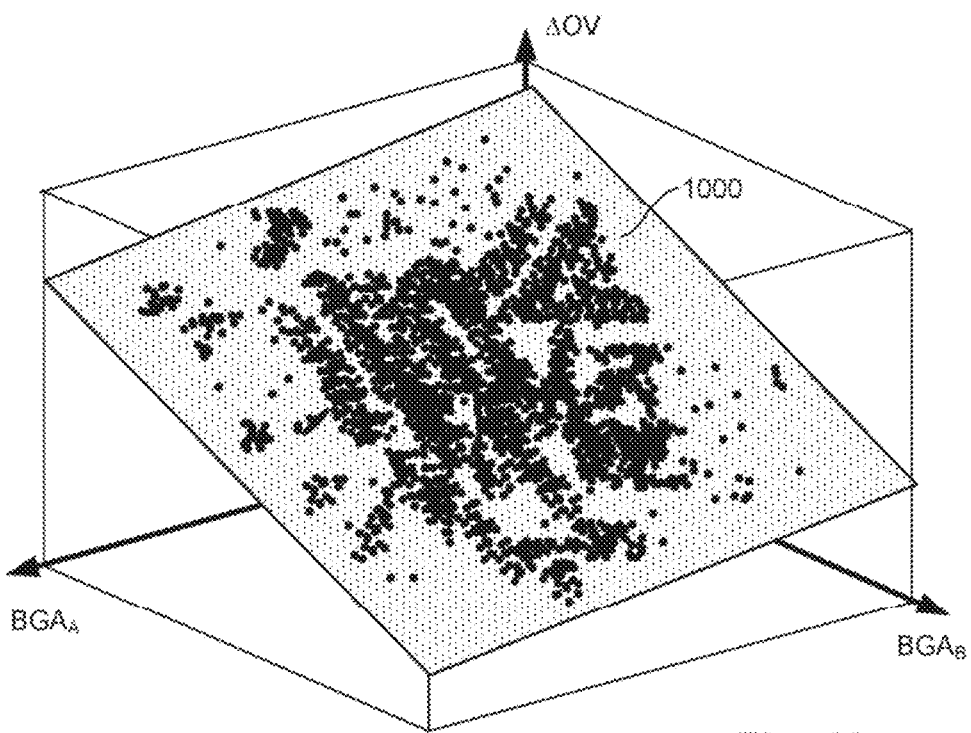
FIG. 12 schematically illustrates an example of a 3-dimensional plot constructed during a step of the method of FIG. 11.

FIG. 12 shows an example of such a 3D plot. It comprises the overlay difference between measurement recipes $\Delta OV$ on the z-axis, and the measurements of structural asymmetry in the first structures $BGA_A$ and $BGA_B$ on the x and y axes respectively. As can be seen, there is good flat plane correlation between $\Delta OV$ and structural asymmetry measurements $BGA_A$ and $BGA_B$ of all the targets, the relationship defining an essentially flat plane 1000. This good correlation indicates that the relationship functions $\xi_{BGA,A}$ and $\xi_{BGA,B}$ are each a constant and therefore can be determined accurately.

At step 930, the relationship functions $\xi_{BGA,A}$ and $\xi_{BGA,B}$ are determined. Relationship functions $\xi_{BGA,A}$ and $\xi_{BGA,B}$ can be determined using equation (16) or considering the slope of plane 1000 in both the x and y directions. The overlay measurement accuracy is related to the correlation between $\Delta OV$ and structural asymmetry measurements $BGA_A$ and $BGA_B$. In theory, when the correlation shows a perfectly flat plane, the error caused by structural asymmetry can be completely eliminated and an error-free overlay fingerprint can be obtained. Where the plane is not perfectly flat, the slope error (a measure of non-correlation) can be determined and used as a measure of uncertainty in the overlay measurements.

At step 940 the corrected overlay $OV_{NSA}$, that is the overlay contribution which is independent of structural asymmetry, can be found by:

$$OV_{NSA} = OV_A - \xi_{BGA,A} * BGA_A$$

$$OV_{NSA} = OV_B - \xi_{BGA,B} * BGA_B \quad (17)$$

In addition to or alternatively to structural asymmetry in a target, a stack difference between adjacent periodic structures of a target or between adjacent targets may be a factor that adversely affects the accuracy of measurement, such as overlay measurement. Stack difference may be understood as an un-designed difference in physical configurations between adjacent periodic structures or targets. Stack difference causes a difference in an optical property (e.g., intensity, polarization, etc.) of measurement radiation between the adjacent periodic structures or targets that is due to other than overlay error, other than intentional bias and other than structural asymmetry common to the adjacent periodic structures or targets. Stack difference includes, but is not limited to, a thickness difference between the adjacent periodic structures or targets (e.g., a difference in thickness of one or more layers such that one periodic structure or target is higher or lower than another periodic structure or target designed to be at a substantially equal level), a refractive index difference between the adjacent periodic structures or targets (e.g., a difference in refractive index of one or more layers such that the combined refractive index for the one or more layers for one periodic structure or target is different than the combined refractive index for the one or more layers for of another periodic structure or target even though designed to have a substantially equal combined refractive index), a difference in material between the adjacent periodic structures or targets (e.g., a difference in the material type, material uniformity, etc. of one or more layers such that there is a difference in material for one periodic structure or target from another periodic structure or target designed to have a substantially same material), a difference in the grating period of the structures of adjacent periodic structures or targets (e.g., a difference in the grating period for one periodic structure or target from another periodic structure or target designed to have a substantially same grating period), a difference in depth of the structures of adjacent periodic structures or targets (e.g., a difference due to etching in the depth of structures of one periodic structure or target from another periodic structure or target designed to have a substantially same depth), a difference in width (CD) of the features of adjacent periodic structures or targets (e.g., a difference in the width of features of one periodic structure or target from another periodic structure or target designed to have a substantially same width of features), etc. In some examples, the stack difference is introduced by processing steps, such as CMP, layer deposition, etching, etc. in the patterning process. In an embodiment, periodic structures or targets are adjacent if within 200 µm of each other, within 150 µm of each other, within 100 µm of each other, within 75 µm of each other, within 50 µm of each other, within 40 µm of each other, within 30 µm of each other, within 20 µm of each other, or within 10 µm of each other.

FIG. 13 schematically illustrates a situation where no stack difference exists between an embodiment of adjacent periodic structures (e.g., composite grating) of a target. For the sake of simplicity, the structure asymmetry is not considered in this example. Further, in the example of FIGS. 13-16, overlay is considered as the measurement parameter. Appropriate adjustments would be made for different parameter measurements using a target, such as CD, focus, dose, etc.

Figure 13A:
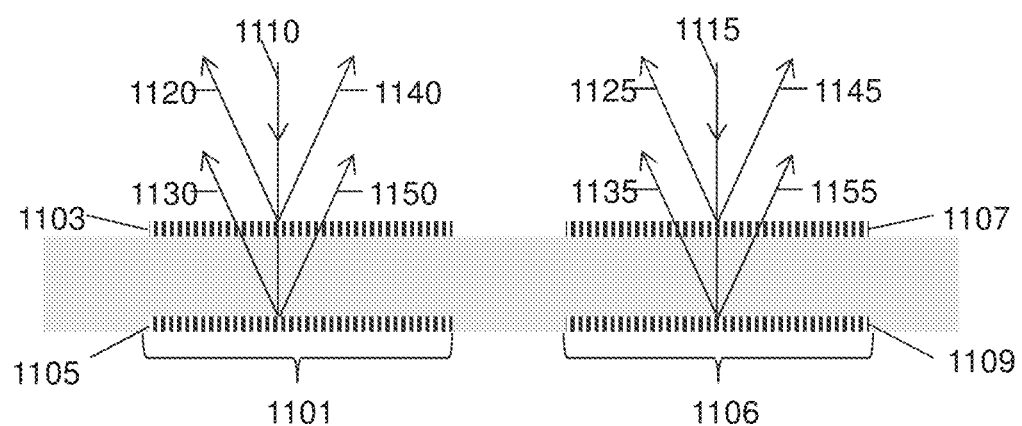
FIG. 13A schematically illustrates a situation where no stack difference exists between a first target periodic structure with a bias +d and a second target periodic structure with a bias −d, and illustrates diffraction signals following diffraction by the first and second target periodic structures.

FIG. 13A shows a first periodic structure 1101 of a target in the form of a composite grating with a bias +d and an adjacent second periodic structure 1106 of the target in the form of a composite grating with a bias −d. A first incident measurement radiation beam 1110 is illuminated on the first structure 1105 and the second structure 1103 of the first periodic structure 1101, where there is a bias +d between the first structure 1105 and the second structure 1103. As a result, $-1^{st}$ diffraction order signals 1130 and 1120 are diffracted by the first structure 1105 and the second structure 1103, respectively. The $-1^{st}$ diffraction order signal diffracted by the first periodic structure 1101, $I'_{-1}{}^{+d}$, may be understood as the combination of the $-1^{st}$ diffraction order signals 1130 and 1120. Additionally, $+1^{st}$ diffraction order signals 1150 and 1140 are diffracted by the first structure 1105 and the second structure 1103, respectively. The $+1^{st}$ diffraction order signal diffracted by the first periodic structure 1101, $I'_{+1}{}^{+d}$, may be understood as the combination of the $+1^{st}$ diffraction order signals 1150 and 1140. Accordingly, the $-1^{st}$ diffraction order signal diffracted by the first periodic structure 1101, $I'_{-1}{}^{+d}$, and the $+1^{st}$ diffraction order signal diffracted by the first periodic structure 1101, $I'_{+1}{}^{+d}$, may be collectively expressed by:

$$I'_{\pm 1}{}^{+d} = 1 + C * \cos(\beta \pm \alpha_+) \quad (18)$$

where C indicates the contrast of the signal (which is a function of the periodic structure design, measurement wavelength, etc.), $$\beta = 4\pi \frac{T}{\lambda},$$

T is the thickness of the first periodic structure, λ is the measurement radiation wavelength, phase term $$\alpha_+ = 2\pi \frac{OV + d}{P},$$

Figures 13B, 13C:
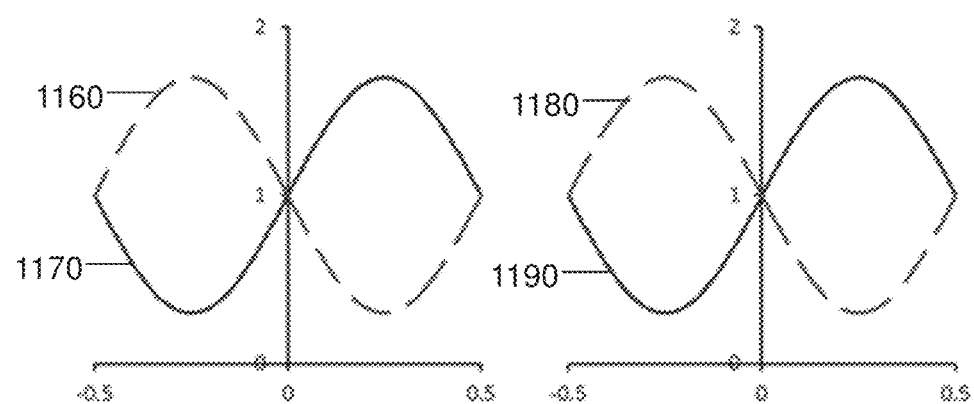
FIG. 13B schematically illustrates the intensity variations of the combined +1$^{st}$ diffraction order signal and the combined −1$^{st}$ diffraction order signal diffracted by the first target periodic structure.
FIG. 13C schematically illustrates the intensity variations of the combined +1$^{st}$ diffraction order signal and the combined −1$^{st}$ diffraction order signal diffracted by the second target periodic structure.

OV is the actual overlay (due to any unintentional misalignment of the layers), and P is the pitch of the first structure 1105 and the second structure 1103 of the first periodic structure 1101. In FIG. 13B, the intensity profiles of the $-1^{st}$ diffraction order signal diffracted by the first periodic structure 1101, $I'_{-1}{}^{+d}$, and the $+1^{st}$ diffraction order signal diffracted by the first periodic structure 1101, $I'_{+1}{}^{+d}$ are depicted in traces 1160 and 1170, respectively according to equation (18).

Similarly, a second incident measurement radiation beam 1115 is illuminated on the first structure 1109 and the second structure 1107 of the second periodic structure 1106, where there is a bias −d between the first structure 1109 and the second structure 1106. As a result, $-1^{st}$ diffraction order signals 1135 and 1125 are diffracted by the first structure 1109 and the second structure 1107 of the second periodic structure 1106, respectively. The $-1^{st}$ diffraction order signal diffracted by the second periodic structure 1106, $I'_{-1}{}^{-d}$, may be understood as the combination of the $-1^{st}$ diffraction order signals 1135 and 1125. Additionally, $+1^{st}$ diffraction order signals 1155 and 1145 are diffracted by the first structure 1109 and the second structure 1107, respectively. The +1$^{st}$ diffraction order signal diffracted by the second periodic structure 1106, $I'_{+1}{}^{-d}$, may be understood as the combination of the +1$^{st}$ diffraction order signals 1155 and 1145. Accordingly, the −1$^{st}$ diffraction order signal diffracted by the second periodic structure 1106, $I'_{-1}{}^{-d}$, and the +1$^{st}$ diffraction order signal diffracted by the second periodic structure 1106, $I'_{+1}{}^{-d}$, may be collectively expressed by:

$$I'_{\pm 1}{}^{-d} = 1 + C^* \cos(\beta \pm \alpha_-) \qquad (19)$$

where C indicates the contrast of the respective signal $$\beta = 4\pi \frac{T}{\lambda},$$

T is the thickness of the second periodic structure, λ is the measurement radiation wavelength, phase term $$\alpha_- = 2\pi \frac{OV - d}{P},$$

OV is the actual overlay (due to any unintentional misalignment of the layers), and P is the pitch of the first structure 1109 and the second structure 1107 of the second periodic structure 1106. In FIG. 13C, the intensity profiles of the −1$^{st}$ diffraction order signal diffracted by the second periodic structure 1106, $I'_{-1}{}^{-d}$, and the +1$^{st}$ diffraction order signal diffracted by the second periodic structure 1106, $I'_{+1}{}^{-d}$, are depicted in traces 1180 and 1190, respectively according to equation (19).

Now, FIG. 14 illustrates a situation where a stack difference exists between a first periodic structure 1201 with a bias +d and an adjacent second periodic structure 1206 with a bias −d. In this case, the stack difference is a different in thickness as shown in FIG. 14A and described hereafter. Similar to FIG. 13, a first incident measurement radiation beam 1210 is illuminated on the first structure 1205 of the first periodic structure 1201 and the second structure 1203 of the first periodic structure 1201, respectively. As a result, −1$^{st}$ diffraction order signals 1230 and 1220 are diffracted by the first structure 1205 and the second structure 1203, respectively. Accordingly, the −1$^{st}$ diffraction order signal diffracted by the first periodic structure 1201, $I_{-1}{}^{-d}$, may be understood as the combination of the −1$^{st}$ diffraction order signals 1230 and 1220. Additionally, +1$^{st}$ diffraction order signals 1250 and 1240 are diffracted by the first structure 1205 and the second structure 1203, respectively. Accordingly, the +1st diffraction order signal diffracted by the first periodic structure 1201, $I_{+1}{}^{-d}$, may be understood as the combination of the +1$^{st}$ diffraction order signals 1250 and 1240.

Similarly, a second incident measurement radiation beam 1215 is illuminated on the first structure 1209 and the second structure 1207 of the second periodic structure 1206, respectively. As a result, −1$^{st}$ diffraction order signals 1235 and 1225 are diffracted by the first structure 1209 and the second structure 1207, respectively. Accordingly, the −1$^{st}$ diffraction order signal diffracted by the second periodic structure 1206, $I_{-1}{}^{+d}$, may be understood as the combination of the −1$^{st}$ diffraction order signals 1225 and 1235. Additionally, +1$^{st}$ diffraction order signals 1255 and 1245 are diffracted by the first structure 1209 and the second structure 1207, respectively. Accordingly, the +1$^{st}$ diffraction order signal diffracted by the second periodic structure 1206, $I_{+1}{}^{+d}$, may be understood as the combination of the +1$^{st}$ diffraction order signals 1255 and 1245.

Figure 14A:
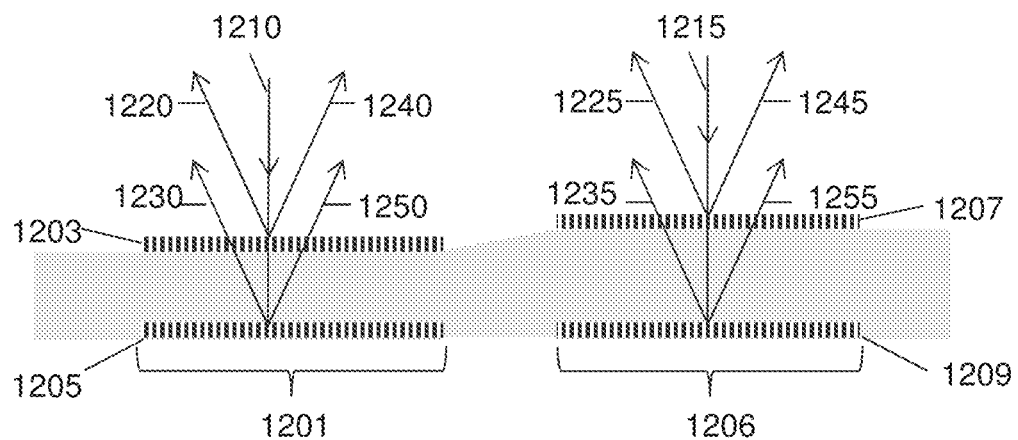
FIG. 14A schematically illustrates a situation where a stack difference exists between a first target periodic structure with a bias +d and a second target periodic structure with a bias −d, and illustrates diffraction signals following diffraction by the first and second target periodic structures.

As an example of stack difference, the first periodic structure 1201 and the second periodic structure 1206 may have a difference in thickness as shown in FIG. 14A. However, in another example, the stack difference may be created by one or more other factors that allow for an additional or alternative difference in un-designed physical configuration between the first periodic structure 1201 and the second periodic structure 1206. For example, a stack difference may be created when the first periodic structure 1201 is more opaque to the first measurement radiation beam 1210 than the second periodic structure 1206. For example, there may be a difference in material (e.g., a same type of material having a different refractive index, a different type of material, etc.) between the first periodic structure 1201 and the second periodic structure 1206. As another example, there may be a difference in pitch of the first periodic structure 1201 relative to the second periodic structure 1206 even though they are designed to have substantially the same pitch. These examples of stack difference are not the only ways there can be a stack difference and so should not be considered as limiting.

Referring back to equations (18) and (19), the stack difference may introduce three additional terms in each of equations (18) and (19). The first term, $\Delta I_N$, indicates an actual change to the intensity of the respective signal. The second term, $\Delta C_N$, indicates an actual change to the contrast of the respective signal. The third term, $\Delta \beta$, indicates an actual change to the phase of the respective signal. The three terms are dependent on the wavelength and/or the polarization of the measurement radiation beams 1210 and 1215. So, in the presence of a stack difference, the −1$^{st}$ diffraction order signal diffracted by the first periodic structure 1201, $I_{-1}{}^{+d}$, and the +1$^{st}$ diffraction order signal diffracted by the first periodic structure 1201, $I_{+1}{}^{+d}$, may be collectively expressed by:

$$I_{\pm 1}{}^{+d} = (1+\Delta I_N)^* \{1 + C^*(1+\Delta C_N)^* \cos[(\beta+\Delta\beta)\pm\alpha_+]\} \qquad (20)$$

Figures 14B, 14C:
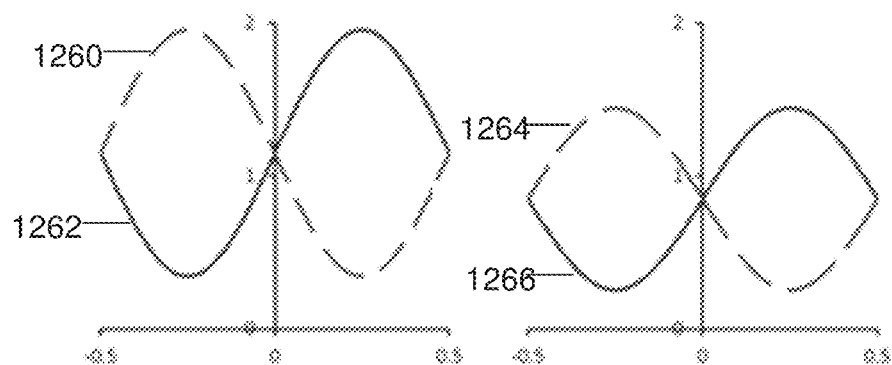
FIG. 14B and FIG. 14C schematically illustrates intensity variations of the combined +1$^{st}$ diffraction order signal and the combined −1$^{st}$ diffraction order signal diffracted by the first target periodic structure and the second target periodic structure, respectively.

In FIG. 14B, the intensity profiles of the −1$^{st}$ diffraction order signal diffracted by the first periodic structure 1201, $I_{-1}{}^{+d}$, and the +1$^{st}$ diffraction order signal diffracted by the first periodic structure 1201, $I_{+1}{}^{+d}$, are depicted in traces 1260 and 1262, respectively according to equation (20).

Figures 14D, 14E:
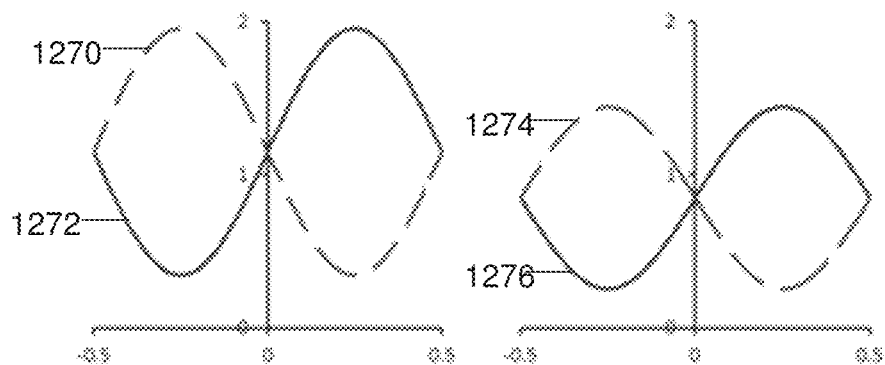
FIG. 14D and FIG. 14E illustrate contrast variations of the combined +1$^{st}$ diffraction order signal and the combined −1$^{st}$ diffraction order signal diffracted by the first target periodic structure and the second target periodic structure, respectively.

In FIG. 14D, the contrast profiles of the −1$^{st}$ diffraction order signal diffracted by the first periodic structure 1201, $I_{-1}{}^{+d}$, and the +1$^{st}$ diffraction order signal diffracted by the first periodic structure 1201, $I_{+1}{}^{+d}$, are depicted in traces 1270 and 1272, respectively according to equation (20).

Figures 14F, 14G:
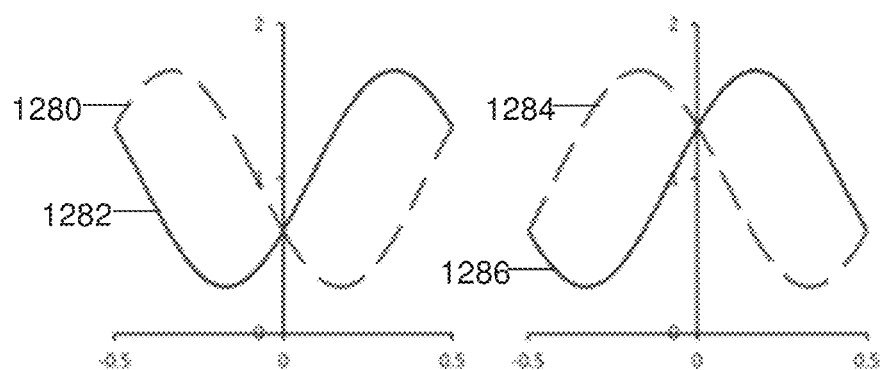
FIG. 14F and FIG. 14G illustrate phase variations of the combined +1$^{st}$ diffraction order signal and the combined −1$^{st}$ diffraction order signal diffracted by the first target periodic structure and the second target periodic structure, respectively.

In FIG. 14F, the phase profiles of the −1$^{st}$ diffraction order signal diffracted by the first periodic structure 1201, $I_{-1}{}^{+d}$, and the +1$^{st}$ diffraction order signal diffracted by the first periodic structure 1201, $I_{+1}{}^{+d}$, are depicted in traces 1280 and 1282, respectively according to equation (20).

Further, in the presence of the stack difference, the −1$^{st}$ diffraction order signal diffracted by the second periodic structure 1206, $I_{-1}{}^{-d}$, and the +1$^{st}$ diffraction order signal diffracted by the second periodic structure 1206, $I_{+1}{}^{-d}$, may be collectively expressed by:

$$I_{\pm 1}{}^{-d}(1-\Delta I_N)^* \{1+C^*(1-\Delta C_N)^* \cos[(\beta-\Delta\beta)\pm\alpha_-]\} \qquad (21)$$

In FIG. 14C, the intensity profiles of the −1$^{st}$ diffraction order signal diffracted by the second periodic structure 1206, $I_{-1}{}^{-d}$, and the +1$^{st}$ diffraction order signal diffracted by the second periodic structure 1206, $I_{+1}{}^{-d}$, are depicted in traces 1264 and 1266, respectively according to equation (21).

Thus, compared to FIG. 14B, there is an intensity imbalance, which can lead to measurement error.

In FIG. 14E, the contrast profiles of the $-1^{st}$ diffraction order signal diffracted by the second periodic structure 1206, $I_{-1}^{-d}$, and the $+1^{st}$ diffraction order signal diffracted by the second periodic structure 1206, $I_{+1}^{-d}$, are depicted in traces 1274 and 1276, respectively according to equation (21). Thus, compared to FIG. 14D, there is a contrast imbalance, which can lead to measurement error.

In FIG. 14G, the phase profiles of the $-1^{st}$ diffraction order signal diffracted by the second periodic structure 1206, $I_{-1}^{-d}$, and the $+1^{st}$ diffraction order signal diffracted by the second periodic structure 1206, $I_{+1}^{-d}$, are depicted in traces 1284 and 1286, respectively according to equation (21). Thus, compared to FIG. 14F, there is a phase imbalance, which can lead to measurement error.

The measured intensity asymmetry of the first periodic structure 1201, $\Delta I^{+d}$ is defined as:

$$\Delta I^{+d} = I_{+1}^{+d} - I_{-1}^{+d} \tag{22}$$

By incorporating equation (20) into equation (22) and assuming $+\Delta I_N$ and $\Delta C_N$ are small, $\Delta I^{+d}$ can be expressed as:

$$\Delta I^{+d} \approx \frac{4\pi}{P} C(1 + \Delta I_N + \Delta C_N)\sin(\beta + \Delta\beta)(OV + d) \tag{23A}$$

And, the mean intensity $\hat{I}^{+d}$ can be expressed as:

$$\hat{I}^{+d} \approx 1 + \Delta I_N + C(1 + \Delta I_N + \Delta C_N)\cos(\beta + \Delta\beta)\left(q - 4\pi^2 \frac{dxOV}{P^2}\right) \tag{23B}$$

$$\text{where } q = 1 - \frac{2\pi^2}{P^2}(OV^2 + d^2)$$

Similarly, the measured intensity asymmetry of the second periodic structure 1206, $\Delta I^{-d}$, is defined as:

$$\Delta I^{-d} = I_{+1}^{-d} - I_{-1}^{-d} \tag{24}$$

By incorporating equation (21) into equation (24) and assuming $+\Delta I_N$ and $\Delta C_N$ are small, $\Delta I^{-d}$ can be expressed as:

$$\Delta I^{-d} \approx \frac{4\pi}{P} C(1 - \Delta I_N - \Delta C_N)\sin(\beta - \Delta\beta)(OV - d) \tag{25A}$$

And, the mean intensity $\hat{I}^{-d}$ can be expressed as:

$$\hat{I}^{-d} \approx 1 - \Delta I_N + C(1 - \Delta I_N - \Delta C_N)\cos(\beta - \Delta\beta)\left(q + 4\pi^2 \frac{dxOV}{P^2}\right) \tag{25B}$$

The measured overlay $OV_m$ can be calculated by:

$$OV_m = d * \frac{\Delta I^{+d} + \Delta I^{-d}}{\Delta I^{+d} - \Delta I^{-d}} \tag{26}$$

By incorporating equations (22)-(25) into equation (26), an error in overlay measurement $\Delta\varepsilon_{OV}$ can be obtained as:

$$\Delta\varepsilon_{OV} = OV_m - OV \approx d * \left[1 - \left(\frac{OV}{d}\right)^2\right] * [\cot(\beta) * \Delta\beta + \Delta I_N + \Delta C_N] \tag{27}$$

When $\beta \approx 90°$ (for a well-designed target) and the overlay (OV) is small (relative to the bias d), equation (27) may be further simplified as:

$$\Delta\varepsilon_{OV} = OV_m - OV \approx d*(\Delta I_N + \Delta C_N) \tag{28}$$

Further, when the first periodic structure 1201 and the second periodic structure 1206 are well designed with a contrast C equal to or approximately equal to 1, $\Delta C_N$ is approximately equal to zero. Therefore, the measurement error $\Delta\varepsilon_{OV}$ can be further simplified as:

$$\Delta\varepsilon_{OV} = OV_m - OV \approx d*\Delta I_N \tag{29}$$

As can be seen from equations (27)-(29), the measured overlay $OV_m$ differs from the actual overlay OV by a measurement error $\Delta\varepsilon_{OV}$ produced by the stack difference. Thus, accuracy in measurement (e.g., measurement of alignment where the target is used for alignment, measurement of overlay where the target is used for overlay measurement, etc.) can be significantly reduced by correcting for stack difference between the adjacent periodic structures or targets. The measurement error that arises from the stack difference may be corrected with changes to the process of creating or measuring the periodic structures or targets (e.g., process offsets) which are, for example, based on yield (i.e., evaluation of processed devices to determine whether the periodic structures or targets were accurate), evaluation of cross-sections of adjacent periodic structures or targets, or complex measurement and analytical reconstructions. These methods can be slow and/or destructive. They may only be effective to correct a constant process error. Further, variation in stack difference of the adjacent periodic structures or targets may not be effectively solved by cross-sections or yield measurements. Accordingly, there is a desire for, for example, a robust solution of evaluating and correcting for stack difference.

In order to characterize the stack difference, one or more stack difference parameters can be defined. A stack difference parameter is a measure of the un-designed asymmetric physical configuration of the adjacent periodic structures or targets. The stack difference parameters can be used to correct measurements made using the periodic structures or targets. The corrected measurements naturally may be used in creating, qualifying, verifying, etc., for example, devices by a patterning process. Additionally or alternatively, the stack difference parameter (or a parameter derived from the stack difference parameter, such as a corrected measurement) can be used in the (re-)design of one or more of the adjacent periodic structures or targets (e.g., making a change to a layout of the design), may be used in the process of forming one or more of the adjacent periodic structures or targets (e.g., making a change in material, a change in a printing step or condition, etc.), may be used in formulation of the measurement conditions (e.g., make a change in the optical measurement formulation in terms of wavelength, polarization, illumination mode, etc. of the measurement beam), etc. In an embodiment, the stack difference parameter can be determined from evaluating cross-sections of the adjacent periodic structures or targets.

In an embodiment, the stack difference parameter can be determined for lower adjacent gratings of a composite grating by evaluating the lower adjacent gratings before the upper gratings are applied. In an embodiment, the stack difference parameter can be derived from a reconstruction (as described above) of the adjacent periodic structures or targets from optical measurements of the adjacent periodic structures or targets or from cross-sections of the adjacent periodic structures or targets. That is, the physical dimensions, characteristics, materials properties, etc. are reconstructed and the differences between the adjacent periodic structures or targets are determined to arrive at a stack difference parameter.

In an embodiment, the stack difference parameter can be used in association with measured radiation from the adjacent periodic structures or targets to derive, for example, a corrected measurement of a parameter of interest, such as overlay, CD, focus, dose, etc. In an embodiment, the stack difference parameter can be used in a simulation of optical measurement of the adjacent periodic structures or targets to derive, for example, a corrected simulated measurement of a parameter of interest, such as overlay, CD, focus, dose, etc. A Maxwell solver and rigorous coupled-wave analysis (RCWA) can be used to arrive at values of the stack difference parameter and/or a corrected simulated measurement of a parameter of interest.

An embodiment of the stack difference parameter is a periodic structure intensity imbalance (GI) which can be defined as:

$$GI = 2 * \frac{\hat{I}^{+d} - \hat{I}^{-d}}{\hat{I}^{+d} + \hat{I}^{-d}} \quad (30)$$

where $\hat{I}^{+d}$ is the average of the $+1^{st}$ diffraction order intensity signal diffracted by the first periodic structure 1201, $I_{+1}^{+d}$, and $-1^{st}$ diffraction order intensity signal diffracted by the first periodic structure 1201, $I_{-1}^{+d}$. Similarly, $\hat{I}^{-d}$ is the average of the $+1^{st}$ diffraction order intensity signal diffracted by the second periodic structure 1206, $I_{+1}^{-d}$, and $-1^{st}$ diffraction order intensity signal diffracted by the second periodic structure 1206, $I_{-1}^{-d}$. In an embodiment, the periodic structure intensity imbalance (GI) can be a derived version, such as $$\frac{\hat{I}^{+d} - \hat{I}^{-d}}{\hat{I}^{+d} + \hat{I}^{-d}}, \frac{\hat{I}^{+d} + \hat{I}^{-d}}{\hat{I}^{+d} - \hat{I}^{-d}},$$

etc.

By incorporating equations (20) and (21) into equation (30), the periodic structure intensity imbalance GI becomes:

$$GI = 2 * \frac{\Delta I_N - C\sin(\beta)[\Delta\beta + \cot(\beta)(\Delta C_N + \Delta I_N)]}{1 + C\cos(\beta)} - 8\pi^2 \frac{C\cos(\beta)}{1 + C\cos(\beta)} \frac{d * OV}{p^2} \quad (31)$$

In equation (31), the first term is related to the stack difference, and the second term is related to the actual overlay OV. The second term is much smaller than the first term. Particularly, when the recipe is well designed, $\beta \approx 90°$ and the overlay (OV) is small, the impact of the actual overlay OV on the periodic structure intensity imbalance GI becomes negligible since the second term becomes zero. Therefore, the periodic structure intensity imbalance GI is dominated by the stack difference as:

$$GI \approx 2\Delta I_N - 2C\Delta\beta \quad (32)$$

When compared to equation (29), it can be seen that the periodic structure intensity imbalance GI is a good indicator of stack difference between the first periodic structure 1201 and the second periodic structure 1206 and thus a good stack difference parameter. To account for a non-negligible second term, a threshold can be applied to GI to identify whether is a significant stack difference or not. That is, for example, if GI exceeds a threshold, then there is a stack difference and GI can be used; otherwise, if GI is below the threshold, the combination of the first and second terms does not identify a significant stack difference.

Thus, the measurement error $\Delta\varepsilon_{OV}$ can be generally represented in terms of a stack difference parameter SD as:

$$\Delta\varepsilon_{OV} = OV_m - OV = \xi_{SD} * SD \quad (33)$$

where $\xi_{SD}$ is a relationship function between the stack difference parameter and the measurement error for the first periodic structure 1201 and the second periodic structure 1206. In an embodiment, the stack difference parameter is or comprises periodic structure intensity imbalance GI (or derived therefrom). Thus, the measurement error $\Delta\varepsilon_{OV}$ may be denoted as $\Delta\varepsilon_{OV} = \xi_{SD} * GI$.

Further, in an embodiment, $\Delta\varepsilon_{OV}$ can be extended by incorporating structural asymmetry such that $$\Delta\varepsilon_{OV} = OV_m - OV = \xi_{SD} * SD + \xi_{BGA} * BGA \quad (34)$$

where BGA is structural asymmetry in the periodic structures 1201, 1206 and $\xi_{BGA}$ is the relationship function between the structural asymmetry and the measurement error for the periodic structures 1201 and 1206.

In equations (33) and (34), $OV_m$ and SD (where, e.g., SD is periodic structure intensity imbalance GI (or derived therefrom)) can be calculated based on measurements of $I_{\pm 1}(\pm d)$, respectively. Further, the values of $OV_m$, SD, and $\xi_{SD}$ are all dependent on the measurement recipe (e.g., wavelength, polarization, etc.).

In an embodiment, the relationship function $\xi_{SD}$ can be found by measuring the adjacent periodic structures or targets using two different measurement recipes. The relationship function iso may be merely a constant value. In this case:

$$OV_{m,A} - OV = \xi_{SD,A} * SD_A$$

$$OV_{m,B} - OV = \xi_{SD,B} * SD_B$$

$$\Delta OV = OV_{m,A} - OV_{m,B} = \xi_{SD,A} * SD_A - \xi_{SD,B} * SD_B \quad (35)$$

where the subscripts A and B denote terms attributable to measurements made using measurement recipe A (a first measurement recipe) and measurement recipe B (a second measurement recipe) respectively. Specifically, $OV_{m,A}$ and $OV_{m,B}$ are the measured overlays using the measurement recipe A and the measurement recipe B respectively, and $\xi_{SD,A}$ and $\xi_{SD,B}$ are the relationship functions for the first and second periodic structures 1201, 1206 in accordance with the measurement recipe A and the measurement recipe B, respectively. $SD_A$ and $SD_B$ are calculated stack difference parameters based on the measurement of $I_{\pm 1}(\pm d)$ using the measurement recipe A and the measurement recipe B respectively. Further, $\Delta OV$ is the difference between the measured overlay with the measurement recipe A, $OV_{m,A}$, and the measured overlay with the measurement recipe B, $OV_{m,B}$. Measurement recipes A and B can differ in, e.g., wavelength and/or polarization of the measurement radiation.

Accordingly, where the stack difference parameter is or comprises periodic structure intensity imbalance GI, equation (35) becomes:

$$OV_{m,A} - OV = \xi_{SD,A} * GI_A$$

$$OV_{m,B} - OV = \xi_{SD,B} * GI_B$$

$$\Delta OV = OV_{m,A} - OV_{m,B} = \xi_{SD,A} * GI_A - \xi_{SD,B} * GI_B \quad (36)$$

where $GI_A$ and $GI_B$ are calculated accordingly to equation (30) based on the measurement of $I_{\pm 1}(\pm d)$ using the measurement recipe A and the measurement recipe B respectively.

Thus, in an embodiment, the relationship function $\xi_{SD}$ can be found by determining the relationship between the calculated stack difference parameter using measurement recipe A, $SD_A$ (e.g., $GI_A$), the calculated stack difference parameter using measurement recipe B, $SD_B$ (e.g., $GI_B$), and the difference in overlay measurements $\Delta OV$ between measurement recipes A and B.

Figure 15:
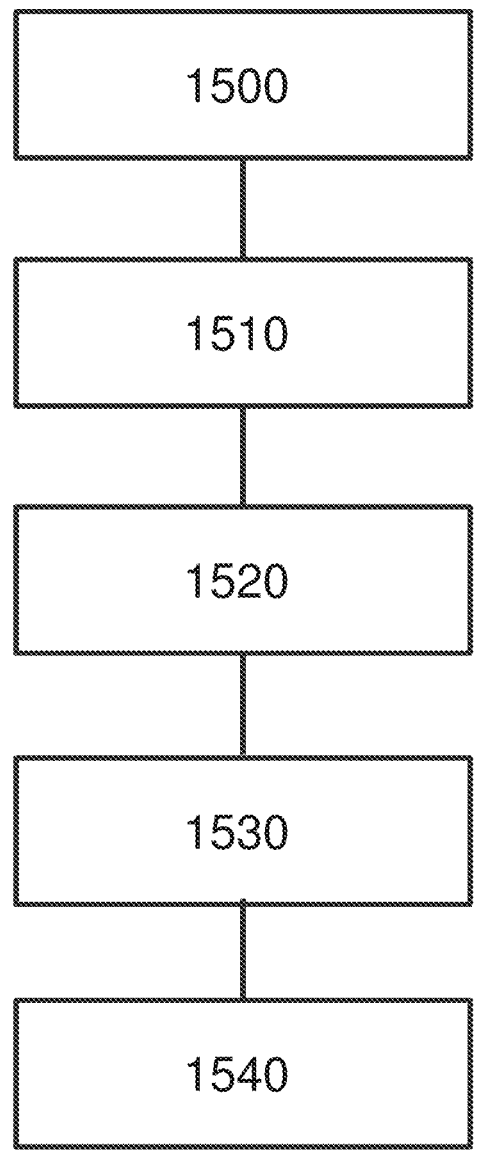
FIG. 15 is a flowchart of steps of a method according to an embodiment.

FIG. 15 is a flowchart of a method of determining the relationship function for the stack different parameter and determining a patterning process parameter (e.g., overlay) according to an exemplary embodiment. The method may be performed by the processor PU in FIG. 3.

At step 1500, intensity measurements of $+1^{st}$ and $-1^{st}$ diffraction order radiation beams diffracted at a plurality of locations of first periodic structures 1201, $I_{\pm 1}^{+d}$, on a substrate and $+1^{st}$ and $-1^{st}$ diffraction order radiation beams diffracted at a plurality of locations of second periodic structures 1206, $I_{\pm 1}^{-d}$, on the substrate are obtained using measurement recipe A and measurement recipe B, respectively.

At step 1510, stack difference parameters $SD_A$ and $SD_B$ and measured overlays $OV_{m,A}$ and $OV_{m,B}$ are determined based on the intensity measurements $I_{\pm 1}(\pm d)$ with measurement recipe A and measurement recipe B, respectively. In an embodiment, the periodic structure imbalance GI is evaluated as the stack difference parameter SD. In this case, the stack difference parameters $SD_A$ (i.e., $GI_A$) and $SD_B$ (i.e., $GI_B$) are determined according to, for example, equation (30) based on the intensity measurements $I_{\pm 1}(\pm d)$ with measurement recipe A and measurement recipe B, respectively.

Similarly, the measured overlays $OV_{m,A}$ and $OV_{m,B}$ are determined according to, for example, equation (26) based on the intensity measurements $I_{\pm 1}(\pm d)$ with measurement recipe A and measurement recipe B, respectively.

At step 1520, a 3D plot may be constructed by plotting $\Delta OV$ (i.e., a difference between $OV_{m,A}$ and $OV_{m,B}$) against the stack difference parameters $SD_A$ (e.g., $GI_A$), on one axis and $SD_B$ (e.g., $GI_B$) on another axis. In an embodiment, an actual plot need not be made but rather the data can be analyzed in such a 3D fashion.

Figure 16:
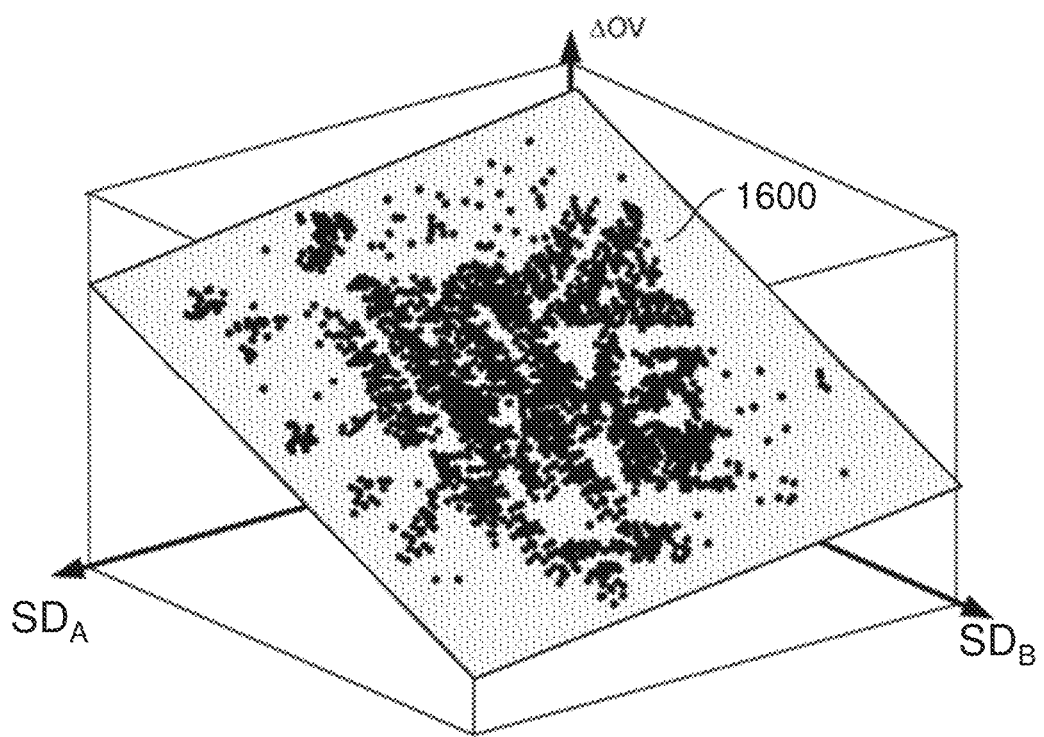
FIG. 16 illustrates an example of a 3-dimensional plot constructed during a step of the method of FIG. 15.

FIG. 16 shows an example of such a 3D plot. It comprises the overlay difference between measurement recipes $\Delta OV$ on the Z-axis, and the measurements of the stack difference parameters $SD_A$ (e.g., $GI_A$), and $SD_B$ (e.g., $GI_B$) on the X and Y axes respectively. In an embodiment, there is good flat plane correlation between $\Delta OV$ and $SD_A$ (e.g., $GI_A$), and $SD_B$ (e.g., $GI_B$); the relationship defines an essentially flat plane 1600.

At step 1530, the relationship functions $\xi_{SD,A}$ and $\xi_{SD,B}$ are determined. Relationship functions $\xi_{SD,A}$ and $\xi_{SD,B}$ can be determined using equation (36), finding a fit in the data $SD_A$, $SD_B$ and $\Delta OV$, or considering the slope of plane 1600 relative to an axis of $SD_A$ and an axis of $SD_B$ in the 3D plot. The overlay measurement accuracy is related to the correlation between $\Delta OV$ and the stack difference parameters $SD_A$ (e.g., $GI_A$), and $SD_B$ (e.g., $GI_B$). In theory, when the correlation shows a perfectly flat plane, the error caused by the stack difference can be completely eliminated and an error-free overlay fingerprint can be obtained. Where the plane is not perfectly flat, the slope error (a measure of non-correlation) can be determined and used as a measure of uncertainty in the overlay measurements.

At step 1540, a corrected overlay OV, that is the overlay contribution which is independent of stack difference, can be found by:

$$OV = OV_{m,A} - \xi_{SD,A} * SD_A$$

$$OV = OV_{m,B} - \xi_{SD,B} * SD_B \quad (37)$$

Also disclosed is a method of identifying desirable target designs and desirable combinations of target design and measurement recipe. In this way, for example, a desirable target design with corresponding desirable measurement recipe A and measurement recipe B can be identified. Once identified, the combination(s) can be used in performing overlay measurements.

It should be noted that one or more desirable measurement recipes will tend to correspond to a particular target design, such that a desirable combination of target design and measurement recipe(s) is identified. So, a particular target design will not necessarily provide good results for all measurement recipes, and one or more particular measurement recipes will not necessarily provide good results for all target designs. However, methods of target design selection optimization which are independent of the measurement recipe are also described.

Target designs may be varied in a number of ways. There may be variation in one or more parameters such as critical dimension, sidewall angle, or pitch, for example. A number of candidate target designs may be evaluated, each showing variation in one or more of these parameters.

Measurement recipes may be varied in terms of parameters such as wavelength and/or polarization. Different candidate measurement recipes (including measurement recipe pairs) may be evaluated, each recipe showing variation in one or more of these parameters (e.g., for one or both of measurement recipes comprised within a pair).

Figure 17:
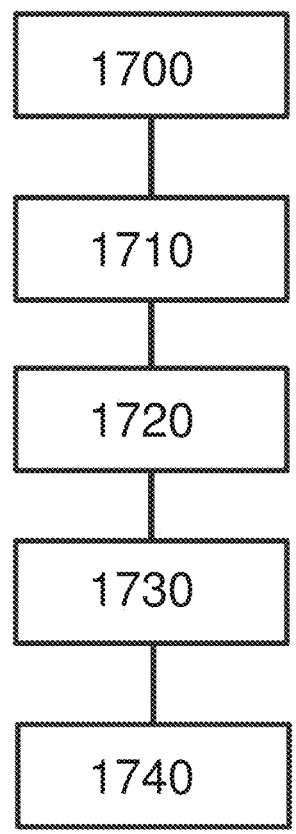
FIG. 17 is a flowchart of steps of a method according to an embodiment.

FIG. 17 is a flowchart of a method of optimizing target design selection according to an exemplary embodiment. The steps of the method are as follows, and are then described in greater detail thereafter:

1700—Measure a plurality of candidate target designs with a plurality of candidate measurement recipe pairs;

1710—Plot a plurality of parameters and $\Delta OV$ on a 3D plot for each combination of candidate target design and candidate measurement recipe pair;

1720—Identify combinations with good correlation;

1730—Identify a desirable combination from flat plane and/or slope uncertainty for each identified combination; and

1740—Identify a desirable measurement recipe from the desirable combination.

At step 1700 a plurality of candidate target designs are devised and multiple samples of each candidate target design are measured. These multiple samples of a plurality of candidate target designs may be measured from a single substrate or a number of substrates. Measurements of each set of samples of each candidate target design may then be acquired for a number of candidate measurement recipe pairs (i.e., for a plurality of different measurement recipe A and/or measurement recipe B).

At step 1710, plots similar to that illustrated in FIG. 16 and described at step 1520 are made for each combination of candidate target design and candidate measurement recipe pair for $\Delta OV$ and stack difference parameters $SD_A$ and $SD_B$. As discussed, further below, plots similar to that illustrated in FIG. 12 and described at step 920 can be made for each combination of candidate target design and candidate measurement recipe pair for ΔOV and the structural asymmetry parameters $BGA_A$ and $BGA_B$.

At step 1720, the combinations which show the highest correlation between ΔOV and the stack difference parameters $SD_A$ and $SD_B$ are identified. This can be achieved by determining the correlation coefficient(s) based on ΔOV and stack difference parameters $SD_A$ and $SD_B$ for each combination and selecting the one or more combinations for which the correlation coefficient is highest. The correlation calculation may be a R2 correlation. Identification of the one or more combinations can be made on the basis of a threshold (e.g., all combinations with a correlation coefficient above a threshold value) or on the basis of a predetermined number of combinations to be selected (e.g., selecting the 10 or 20 combinations having the highest correlation). If only one combination shows a good correlation, then this can be selected without performing the next step 1730. However, performance of step 1730 is desirable as this can determine whether this one combination has a suitable flat plane correlation. If not, then it may be desirable to begin again with one or more different candidate target designs and/or one or more candidate measurement recipe pairs.

Step 1720 may optionally comprise identifying a target design which can be seen to outperform other target designs over the range of candidate measurement recipe pairs in the correlation determination. For example, a desirable target design may be identified if it shows good correlation for a greater number of measurement recipe pairs, or a better average correlation over the range of candidate measurement recipe pairs, compared to the other target designs.

At step 1730, the combinations selected at step 1720 are further evaluated. In particular, it should be appreciated that a high coefficient of correlation does not, in itself, indicate an ideal combination. Even where there is a high coefficient of correlation between ΔOV, $SD_A$ and $SD_B$, there may also be a strong inter-dependence between stack difference parameters $SD_A$ and $SD_B$. In such a case the 3D plot will tend to form a line, rather than a plane. This results in a large slope uncertainty (which is a measure of non-correlation) due to the freedom of rotation around the line axis. Therefore it is desirable that combinations are identified which do not show this inter-dependency between the stack difference parameters $SD_A$ and $SD_B$ for the two recipes (or for which this inter-dependency is smallest).

Consequently, at step 1730, the combination which shows the best flat plane correlation is selected. This combination can be identified by considering the 3D-plots of the combinations which show a high correlation and determining whether the points on the plot define an essentially flat plane (rather than a line). The combination for which its plot better defines an essentially flat plane can then be selected. If this yields a combination which demonstrates a clearly better flat plane correlation then this candidate measurement recipe combination can be selected as the desirable combination. If there are still a number of combinations for which the determined flat plane correlation is similar or at an acceptable level, then another evaluation metric can be used. Such an evaluation metric may be the slope uncertainty of each plot. The slope uncertainty is a measure of overlay uncertainty. It is possible to use this uncertainty in the overlay measurements as an index of measurement recipe selection. Such a method may comprise fitting the plane of the 3D plot to the data points which comprise confidence bounds (thereby defining a confidence range for each point). Purely by way of example, it may be assumed that each data point has a 95% confidence bound. This will provide a measure of the slope uncertainty and therefore the overlay uncertainty. Multiplying a stack difference SD by the confidence range will yield the uncertainty of the correction.

Optionally, the evaluation in steps 1710-1730 can additionally or alternatively be performed for identifying combinations which show the highest correlation between ΔOV and the structural asymmetry parameters $BGA_A$ and $BGA_B$. This evaluation for structural asymmetry can be performed at the same time or precede/succeed the evaluation for stack difference. Desirably, the evaluation for structural asymmetry is performed together with the evaluation for stack difference to co-optimally find one or more target design and measurement recipe(s) combinations with highest correlation of stack difference and structural asymmetry to ΔOV.

Step 1730 should identify a combination of target design and measurement recipe pair which is optimized for overlay measurement in terms of stack difference and/or structural asymmetry. Therefore this method may be used to optimize selection of target design and measurement recipe pair for the method of FIG. 15 and/or FIG. 11.

At optional step 1740, one of the measurement recipes of the measurement recipe pair identified at step 1730 may be chosen to be a desirable measurement recipe for overlay measurements where only measurement with one measurement recipe is possible or desirable (e.g., to maximize throughput). This desirable measurement recipe may be the recipe of the pair for which the corresponding stack differences and/or structural asymmetries is smallest. Lower stack differences and/or structural asymmetries will result in less correction, so the measured overlay should be closer to real overlay. The desirable recipe will correspond to the desirable target design.

In an embodiment, instead of constructing a 3-dimensional plot as described herein, a 2-dimensional plot can be constructed. In an embodiment, the 2-dimensional plot will be a plot of ΔOV against ΔSD, where ΔSD is the difference between $SD_A$ and $SD_B$ and/or a plot of ΔOV against ΔBGA, where ΔBGA is the difference between $BGA_A$ and $BGA_B$. The correlation between ΔOV and ΔSD and/or between ΔOV and ΔBGA can then be determined from the plot and, if there is sufficient correlation, the corrected overlay OV can be determined. For there to be a straight line correlation between ΔOV and ΔSD and between ΔOV and ΔBGA, it must be the case that relationship functions $\xi_{SD,A}$ and $\xi_{SD,B}$ (i.e. $\xi_{SD,A} = \xi_{SD,B} = \xi_{SD}$) are the same and the relationship functions $\xi_{BGA,A}$ and $\xi_{BGA,B}$ (i.e. $\xi_{BGA,A} = \xi_{BGA,B} = \xi_{BGA}$) are the same. Where this is the case, the slope of the applicable line provides the relationship function $\xi_{SD} = \xi_{SD,A} = \xi_{SD,B}$ or $\xi_{BGA} = \xi_{BGA,A} = \xi_{BGA,B}$. As before, the corrected overlay can then be calculated as already described using, for example, equation (37) and/or equation (17). As with the 3D plot method, identification of desired target designs and combinations of target designs and measurement recipe pairs can be identified by identifying those plots which show the best correlation or least slope uncertainty (of the line).

In summary, the following are features made possible by the concepts described herein:

Feed forward stack difference and optionally structural asymmetry characterization for correction of overlay error measurements in inline measurement;

More accurate overlay measurements can be obtained from overlay and stack difference and/or structural asymmetry determinations using two (or more) recipes via a simple and direct method;

Process-robust target and measurement recipe combinations can be identified using two recipes which having strong linear correlation between stack difference/structural asymmetry and differences in measured overlay error; and A desirable recipe can be determined from calculated stack difference/structural asymmetry and overlay error uncertainty.

Theoretically, the methods described herein can completely remove errors caused by stack difference and optionally structural asymmetry. The methods described herein may require no new reticle design, no change in metrology design and/or no increase in metrology target real-estate. The methods are also capable of broader application, for example, the stack difference and/or structural asymmetry can be used for process stability monitoring.

Figure 18:
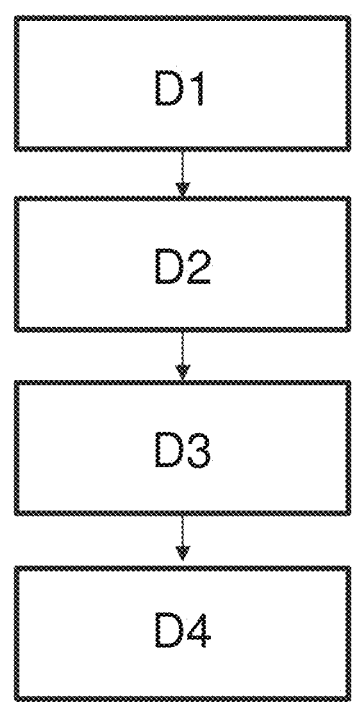
FIG. 18 is a flowchart illustrating a process in which the metrology target is used to monitor performance, and as a basis for controlling metrology, design and/or production processes.

FIG. 18 shows a flowchart illustrating a process in which the metrology target is used to monitor performance, and as a basis for controlling metrology, design and/or production processes. In step D1, substrates are processed to produce product features and one or more metrology targets as described herein. At step D2, patterning process parameter (e.g., overlay) values are measured and calculated using, e.g., the method of FIG. 6 and optionally, corrected using the asymmetry and/or stack difference parameter. At step D3, the measured patterning process parameter (e.g., overlay) value may be used (together with other information as may be available), to update a metrology recipe. The updated metrology recipe is used for re-measurement of the patterning process parameter, and/or for measurement of the patterning process parameter on a subsequently processed substrate. In this way, the calculated patterning process parameter is improved in accuracy. The updating process can be automated if desired. In step D4, the patterning process parameter value is used to update a recipe that controls the lithographic patterning step and/or other process step in the device manufacturing process for re-work and/or for processing of further substrates. Again this updating can be automated if desired.

While the embodiments disclosed above are described in terms of diffraction based overlay measurements (e.g., measurements made using the second measurement branch of the apparatus shown in FIG. 3A), in principle the same models can be used for pupil based overlay measurements (e.g., measurements made using the first measurement branch of the apparatus shown in FIG. 3A). Consequently, it should be appreciated that the concepts described herein are equally applicable to diffraction based overlay measurements and pupil based overlay measurements.

While embodiments of the metrology target described herein have mostly been described in the terms of overlay measurement, embodiments of the metrology target described herein may be used to measure one or more additional or alternative patterning process parameters. For example, the metrology target may be used to measure exposure dose variation, measure exposure focus/defocus, measure CD, etc. Further, the description here may also apply, with modifications as appropriate, to, e.g., substrate and/or patterning device alignment in a lithographic apparatus using an alignment mark. Similarly, the appropriate recipe for the alignment measurement may be determined.

While the target structures described above are metrology targets specifically designed and formed for the purposes of measurement, in other embodiments, properties may be measured on targets which are functional parts of devices formed on the substrate. Many devices have regular, periodic structures akin to a grating. The term "target", "grating" or "periodic structure" of a target as used herein does not require that the applicable structure has been provided specifically for the measurement being performed. Further, pitch P of the metrology target is close to the resolution limit of the optical system of the measurement tool, but may be much larger than the dimension of typical product features made by a patterning process in the target portions C. In practice the features and/or spaces of the periodic structures may be made to include smaller structures similar in dimension to the product features.

In association with the physical structures of the targets as realized on substrates and patterning devices, an embodiment may include a computer program containing one or more sequences of machine-readable instructions and/or functional data describing the target design, describing a method of designing a target for a substrate, describing a method of producing a target on a substrate, describing a method of measuring a target on a substrate and/or describing a method of analyzing a measurement to obtain information about a patterning process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein. Where an existing inspection apparatus, for example of the type shown in FIG. 3, is already in production and/or in use, an embodiment can be implemented by the provision of an updated computer program product for causing a processor to perform one or more of the methods described herein (e.g., to perform a modified step S6 and calculate overlay error or other parameters with reduced sensitivity to stack difference and/or structural asymmetry). The program may optionally be arranged to control the optical system, substrate support and the like to perform a method of measuring a parameter of the patterning process on a suitable plurality of targets (e.g., perform steps S2-S5 for measurement of stack difference and/or structural asymmetry on a suitable plurality of targets). The program can update the lithographic and/or metrology recipe for measurement of further substrates. The program may be arranged to control (directly or indirectly) the lithographic apparatus for the patterning and processing of further substrates.

Further, embodiments have been described herein in relation to diffraction-based metrology, which, for example, measures the relative position of overlapping periodic structures from the intensity from the diffracted orders. However, embodiments herein may be applied, with appropriate modification where needed, to image-based metrology, which, for example, measures the relative position from target 1 in layer 1 to target 2 in layer 2 using high-quality images of the targets. Usually these targets are periodic structures or "boxes" (Box-in-Box (BiB)).

In an embodiment, there is provided a method comprising: obtaining a measurement of a metrology target on a substrate processed using a patterning process, the measurement having been obtained using measurement radiation; and deriving a parameter of interest of the patterning process from the measurement, wherein the parameter of interest is corrected by a stack difference parameter, the stack difference parameter representing an un-designed difference in physical configuration between adjacent periodic structures of the target or between the metrology target and another adjacent target on the substrate.

In an embodiment, deriving the parameter of interest comprising correcting a measured value of the parameter of interest using the stack difference parameter and a relationship function. In an embodiment, deriving the parameter of interest further comprising correcting a measured value of the parameter of interest using a structural asymmetry parameter. In an embodiment, the stack difference parameter comprises a periodic structure intensity imbalance. In an embodiment, the periodic structure intensity imbalance is a function of (i) the difference between the average intensity of measurement radiation from the first adjacent periodic structure or target and the average intensity of measurement radiation from the second adjacent periodic structure or target, and (ii) the addition of an average intensity of measurement radiation from a first adjacent periodic structure or target with an average intensity of measurement radiation from a second adjacent periodic structure or target. In an embodiment, wherein the periodic structure intensity imbalance comprises value of (i) divided by the value of (ii). In an embodiment, periodic structures or targets are adjacent if within 200 μm of each other. In an embodiment, the metrology target comprises adjacent periodic structures and the stack difference parameter represents an un-designed difference in physical configuration between adjacent periodic structures of the target. In an embodiment, the adjacent periodic structures of the metrology target have a different bias. In an embodiment, the different biases have the same absolute value but different signs. In an embodiment, the parameter of interest comprises overlay, critical dimension, focus or dose. In an embodiment, the stack difference is introduced by chemical or mechanical processing step. In an embodiment, the method further comprises: obtaining first values of the stack difference parameter and second values of the stack difference parameter for a plurality of adjacent periodic structures of a measurement target or for a plurality of adjacent measurement targets, the first values of the stack difference parameter and second values of the stack difference parameter having been obtained with, respectively, measurements using first measurement radiation and second measurement; obtaining first values of a target parameter and second values of the target parameter from the plurality of adjacent periodic structures of the measurement target or for the plurality of adjacent measurement targets, the first values of the patterning process parameter and second values of the patterning process parameter having been obtained with, respectively, the first measurement radiation and the second measurement radiation and wherein the patterning process parameter value comprises a part which is independent of the un-designed difference in physical configuration, and a part due to the un-designed difference in physical configuration; determining a relationship function describing the relationship between the first and/or second values of stack difference parameter and the difference of the first values of the patterning process parameter and the second values of the patterning process parameter; and determining a part of the parameter of interest which is independent of the un-designed difference in physical configuration from the relationship function. In an embodiment, the target parameter comprises a measurement beam intensity asymmetry, overlay, critical dimension, focus or dose.

In an embodiment, there is provided method comprising: obtaining first values of a stack difference parameter and second values of a stack difference parameter for a plurality of adjacent periodic structures of a measurement target or for a plurality of adjacent measurement targets, the first values of the stack difference parameter and second values of the stack difference parameter having been obtained with, respectively, measurements using first measurement radiation and second measurement radiation and the stack difference parameter representing an un-designed difference in physical configuration between adjacent periodic structures of a measurement target or between adjacent measurement targets on a substrate; obtaining first values of a target parameter and second values of the target parameter from the plurality of adjacent periodic structures of the measurement target or for the plurality of adjacent measurement targets, the first values of the target parameter and second values of the target parameter having been obtained with, respectively, the first measurement radiation and the second measurement radiation and wherein the target parameter value comprises a part which is independent of the un-designed difference in physical configuration, and a part due to the un-designed difference in physical configuration; determining a relationship function describing the relationship between the first and/or second values of stack difference parameter and the difference of the first values of the target parameter and the second values of the target parameter; and determining a part of a target parameter value which is independent of the un-designed difference in physical configuration from the relationship function.

In an embodiment, the relationship function comprises a constant. In an embodiment, determining the relationship function comprises determining a first relationship function describing a substantially linear relationship between the first values of the stack difference parameter and the difference of the first values of the target parameter and the second values of the target parameter and a second relationship function describing a substantially linear relationship between the second values of the stack difference parameter and the difference of the first values of the target parameter and the second values of the target parameter. In an embodiment, determining the relationship function comprises making a 3-dimensional plot of the difference of the first values of the target parameter and the second values of the target parameter against the first values of the stack difference parameter and against the second values of the stack difference parameter. In an embodiment, data points on the 3-dimensional plot substantially correlate to define an essentially flat plane and wherein a first relationship function is described by a slope of the plane relative to an axis of the first values of the stack difference parameter and a second relationship function is described by a slope of the plane relative to an axis of the second values of the stack difference parameter. In an embodiment, determining the relationship function comprises determining a relationship function which describes a substantially linear relationship between: the difference of the first values of target parameter and the second values of target parameter; and the difference of the first values of stack difference parameter and the second values of stack difference parameter. In an embodiment, determining the relationship function comprises making a plot of the difference of the first values of target parameter and the second values of target parameter against the difference of the first values of stack difference parameter and the second values of stack difference parameter, the relationship function being described by the slope of a line fitted to the plot.

In an embodiment, the method comprises determining a degree of correlation of 1) the first and/or second values of stack difference parameter, and 2) the difference of the first values of target parameter and the second values of target parameter. In an embodiment, a degree of correlation is used in determining a measure of the accuracy of the determined part of a target parameter value which is independent of the un-designed difference in physical configuration. In an embodiment, the method comprises an initial optimization to determine a desired target from a plurality of candidate targets, the initial optimization comprising: obtaining plural sets of values comprising the first and second values of stack difference parameter and the first and second values of target parameter, for multiple samples of a plurality of candidate targets and a plurality of candidate measurement radiation pairs of the first measurement radiation and the second measurement radiation, each set of values relating to a different combination of one of the candidate targets and one of the candidate measurement radiation pairs; determining a degree of correlation for each of the plural sets of values; and selecting a desired target from one of the candidate targets based upon the determined degree of correlation for each set of values. In an embodiment, selecting a desired target comprises: determining for each candidate target, the number of sets of values relating to that candidate target for which the determined degree of correlation is above a threshold; and selecting as the desired target, the candidate target for which the number of sets of values having a determined degree of correlation above a threshold is greatest. In an embodiment, selecting a desired target comprises: determining for each candidate target, an average for the determined degree of correlation for each set of values relating to that candidate target; and selecting as the desired target, the candidate target for which the determined average is greatest. In an embodiment, selecting a desired target comprises selecting a desired combination of one of the candidate targets and one of the candidate measurement radiation pairs based upon the determined degree of correlation for each set of values. In an embodiment, selecting the desired combination comprises selecting the combination corresponding to the set of values for which the determined degree of correlation is highest. In an embodiment, selecting the desired combination comprises selecting a subset of combinations, each of the subset of combinations corresponding to a set of values for which the determined degree of correlation is high. In an embodiment, the subset of combinations comprises all combinations corresponding to a set of values for which the determined degree of correlation is above a threshold. In an embodiment, the method comprises selecting as the desired combination from the subset of combinations, a combination for which the corresponding set of values defines an essentially flat plane on a corresponding plot of the difference of the first values of target parameter and the second values of target parameter against the first values of stack difference parameter and against the second values of stack difference parameter. In an embodiment, the desired combination is that for which the corresponding set of values best defines an essentially flat plane on the plot. In an embodiment, where there is more than one combination for which the corresponding set of values defines an essentially flat plane on the plot to an acceptable degree, the method further comprises: determining a degree of uncertainty for each of these set of values which define an essentially flat plane; and selecting as the desired combination, the combination for which the corresponding set of values has the smallest determined degree of uncertainty. In an embodiment, the determined degree of uncertainty comprises a degree of uncertainty in the first and second values of target parameter. In an embodiment, the desired combination is selected as that which best reduces inter-dependency between the first values of target parameter and the second values of target parameter. In an embodiment, the method comprises selecting either the first measurement radiation or the second measurement radiation of the measurement radiation pair of the desired combination as a desired measurement radiation based on which one results in the smallest value for measurement of the stack difference parameter. In an embodiment, the target parameter is overlay and the part of overlay value which is independent of the un-designed difference in physical configuration comprises a contribution due to a known imposed bias and a contribution due to an overlay error. In an embodiment, the target parameter is measurement beam intensity asymmetry. In an embodiment, the first measurement radiation has a selected characteristic which is different to that of the second measurement radiation, the selected characteristic of the measurement radiation comprising wavelength or polarization. In an embodiment, the method comprises: measuring the adjacent periodic structures or targets using the first measurement radiation to obtain the first values of stack difference parameter; measuring the adjacent periodic structures or targets using the second measurement radiation to obtain the second values of stack difference parameter; measuring the target of the adjacent periodic structures or the targets of the plurality of adjacent targets using the first measurement radiation to obtain the first values of target parameter; and measuring the target of the adjacent periodic structures or the targets of the plurality of adjacent targets using the second measurement radiation to obtain the second values of target parameter. In an embodiment, the measuring comprises: illuminating the adjacent periodic structures or targets with the measurement radiation and detecting the measurement radiation scattered by each periodic structure or target; and measuring intensity asymmetry in corresponding higher orders of the scattered measurement radiation. In an embodiment, the measuring of the adjacent periodic structures or targets is performed prior to formation of a structure overlying the adjacent periodic structures or targets.

In an embodiment, there is provided a method of selecting a target from a plurality of candidate targets, the method comprising: obtaining plural sets of values for a plurality of candidate measurement radiation pairs and a plurality of candidate targets, each candidate target comprising a first periodic structure horizontally adjacent to a second periodic structure, each set of values relating to a different combination of one of the candidate targets and one of the candidate measurement radiation pairs, each set of values comprising, for multiple samples of the candidate target: first values of stack difference parameter and second values of stack difference parameter of the adjacent periodic structures of the candidate target using, respectively, a first measurement radiation and a second measurement radiation of the candidate measurement radiation pair, the stack difference parameter representing an un-designed difference in physical configuration between adjacent periodic structures of a target; first values of target parameter and second values of target parameter of the candidate target using, respectively, the first measurement radiation and the second measurement radiation; for each set of values, determining a degree of correlation between the first and/or second values of stack difference parameter and the difference of the first values of target parameter and the second values of target parameter; and selecting a desired target from one of the candidate targets based upon the determined degree of correlation for each set of values.

In an embodiment, selecting a desired target comprises: determining for each candidate target, the number of sets of values relating to that candidate target for which the determined degree of correlation is above a threshold; and selecting as the desired target, the candidate target for which the number of sets of values having a determined degree of correlation above a threshold is greatest. In an embodiment, selecting a desired target comprises: determining for each candidate target, an average for the determined degree of correlation for each set of values relating to that candidate target; and selecting as the desired target, the candidate target for which the determined average is greatest. In an embodiment, selecting a desired target comprises selecting a desired combination of one of the candidate targets and one of the candidate measurement radiation pairs based upon the determined degree of correlation for each set of values. In an embodiment, selecting a desired combination comprises selecting the combination corresponding to the set of values for which the determined degree of correlation is highest. In an embodiment, selecting a desired combination comprises selecting a subset of combinations, each of the subset of combinations corresponding to a set of values for which the determined degree of correlation is high. In an embodiment, the subset of combinations comprises all combinations corresponding to a set of values for which the determined degree of correlation is above a threshold. In an embodiment, the method comprises selecting as the desired combination from the subset of combinations, a combination for which the corresponding set of values defines an essentially flat plane on a corresponding plot of the difference of the first values of target parameter and the second values of target parameter against the first values of stack difference parameter and against the second values of stack difference parameter. In an embodiment, the desired combination is that for which the corresponding set of values best defines a flat plane on the plot. In an embodiment, where there is more than one combination for which the corresponding set of values defines an essentially flat plane on the plot to an acceptable degree, the method further comprises: determining a degree of uncertainty for each of these set of values which define an essentially flat plane; and selecting as the desired combination, the combination for which the corresponding set of values has the smallest determined degree of uncertainty. In an embodiment, the determined degree of uncertainty comprises a degree of uncertainty in the first and second values of target parameter. In an embodiment, the desired combination is selected as that which best reduces inter-dependency between the first values of target parameter and the second values of target parameter. In an embodiment, the method comprising selecting either of the first measurement radiation or the second measurement radiation of the measurement radiation pair of the desired combination as a desired measurement radiation based on which one results in the smallest value for measurement of stack difference parameter. In an embodiment, the method comprises performing an overlay measurement using the desired measurement radiation on the desired target of the desired combination. In an embodiment, the method comprises performing an overlay measurement using the measurement radiation pair of the desired combination on the desired target of the desired combination. In an embodiment, the method comprises performing an overlay measurement on the desired target. In an embodiment, the target parameter is overlay and the part of overlay value which is independent of the un-designed difference in physical configuration comprises a contribution due to a known imposed bias and a contribution due to an overlay error. In an embodiment, the target parameter is measurement beam intensity asymmetry.

In an embodiment, there is provided a metrology apparatus for measuring a parameter of a lithographic process, the metrology apparatus being operable to perform a method as described herein.

In an embodiment, there is provided a non-transitory computer program product comprising machine-readable instructions for causing a processor to cause performance of a method as described herein.

In an embodiment, there is provided a system comprising: an inspection apparatus configured to provide a beam of radiation on two adjacent periodic structures or measurement targets on a substrate and to detect radiation diffracted by the targets to determine a parameter of a patterning process; and a non-transitory computer program as described herein. In an embodiment, the system further comprises a lithographic apparatus comprising a support structure configured to hold a patterning device to modulate a radiation beam and a projection optical system arranged to project the modulated radiation beam onto a radiation-sensitive substrate.

The term "optimizing" and "optimization" as used herein mean adjusting an apparatus or process, e.g., a lithographic apparatus or an optical lithography process step, such that patterning and/or device fabrication results and/or processes (e.g., of lithography) have one or more desirable characteristics, such as higher accuracy of projection of a design layout on a substrate, larger process window, etc.

An embodiment of the invention may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

One or more aspects disclosed herein may be implanted in a control system. Any control system described herein may each or in combination be operable when the one or more computer programs are read by one or more computer processors located within at least one component of an apparatus. The control systems may each or in combination have any suitable configuration for receiving, processing, and sending signals. One or more processors are configured to communicate with the at least one of the control systems. For example, each control system may include one or more processors for executing the computer programs that include machine-readable instructions for the methods described above. The control systems may include data storage medium for storing such computer programs, and/or hardware to receive such medium. So the control system(s) may operate according the machine readable instructions of one or more computer programs.

Embodiments are described in the below numbered clauses:

1. A method comprising: obtaining a measurement of a metrology target on a substrate processed using a patterning process, the measurement having been obtained using measurement radiation; and deriving a parameter of interest of the patterning process from the measurement, wherein the parameter of interest is corrected by a stack difference parameter, the stack difference parameter representing an un-designed difference in physical configuration between adjacent periodic structures of the target or between the metrology target and another adjacent target on the substrate.

2. The method of clause 1, wherein deriving the parameter of interest comprising correcting a measured value of the parameter of interest using the stack difference parameter and a relationship function.

3. The method of clause 1 or clause 2, wherein deriving the parameter of interest further comprising correcting a measured value of the parameter of interest using a structural asymmetry parameter.

4. The method of any of clauses 1-3, wherein the stack difference parameter comprises a periodic structure intensity imbalance.

5. The method of clause 4, wherein the periodic structure intensity imbalance is a function of (i) the difference between the average intensity of measurement radiation from the first adjacent periodic structure or target and the average intensity of measurement radiation from the second adjacent periodic structure or target, and (ii) the addition of an average intensity of measurement radiation from a first adjacent periodic structure or target with an average intensity of measurement radiation from a second adjacent periodic structure or target.

6. The method of clause 5, wherein the periodic structure intensity imbalance comprises value of (i) divided by the value of (ii).

7. The method of any of clauses 1-6, wherein periodic structures or targets are adjacent if within 200 µm of each other.

8. The method of any of clauses 1-7, wherein the metrology target comprises adjacent periodic structures and the stack difference parameter represents an un-designed difference in physical configuration between adjacent periodic structures of the target.

9. The method of clause 8, wherein the adjacent periodic structures of the metrology target have a different bias.

10. The method of clause 9, wherein the different biases have the same absolute value but different signs.

11. The method of any of clauses 1-10, wherein the parameter of interest comprises overlay, critical dimension, focus or dose.

12. The method of any of clauses 1-11, wherein the stack difference is introduced by chemical or mechanical processing step.

13. The method of any of clauses 1-12, further comprising: obtaining first values of the stack difference parameter and second values of the stack difference parameter for a plurality of adjacent periodic structures of a measurement target or for a plurality of adjacent measurement targets, the first values of the stack difference parameter and second values of the stack difference parameter having been obtained with, respectively, measurements using first measurement radiation and second measurement; obtaining first values of a target parameter and second values of the target parameter from the plurality of adjacent periodic structures of the measurement target or for the plurality of adjacent measurement targets, the first values of the patterning process parameter and second values of the patterning process parameter having been obtained with, respectively, the first measurement radiation and the second measurement radiation and wherein the patterning process parameter value comprises a part which is independent of the un-designed difference in physical configuration, and a part due to the un-designed difference in physical configuration; determining a relationship function describing the relationship between the first and/or second values of stack difference parameter and the difference of the first values of the patterning process parameter and the second values of the patterning process parameter; and determining a part of the parameter of interest which is independent of the un-designed difference in physical configuration from the relationship function.

14. The method of clause 13, wherein the target parameter comprises a measurement beam intensity asymmetry, overlay, critical dimension, focus or dose.

15. A method comprising: obtaining first values of a stack difference parameter and second values of a stack difference parameter for a plurality of adjacent periodic structures of a measurement target or for a plurality of adjacent measurement targets, the first values of the stack difference parameter and second values of the stack difference parameter having been obtained with, respectively, measurements using first measurement radiation and second measurement radiation and the stack difference parameter representing an un-designed difference in physical configuration between adjacent periodic structures of a measurement target or between adjacent measurement targets on a substrate; obtaining first values of a target parameter and second values of the target parameter from the plurality of adjacent periodic structures of the measurement target or for the plurality of adjacent measurement targets, the first values of the target parameter and second values of the target parameter having been obtained with, respectively, the first measurement radiation and the second measurement radiation and wherein the target parameter value comprises a part which is independent of the un-designed difference in physical configuration, and a part due to the un-designed difference in physical configuration; determining a relationship function describing the relationship between the first and/or second values of stack difference parameter and the difference of the first values of the target parameter and the second values of the target parameter; and determining a part of a target parameter value which is independent of the un-designed difference in physical configuration from the relationship function.

16. The method of clause 15, wherein the relationship function comprises a constant.

17. The method of clause 15 or clause 16, wherein determining the relationship function comprises determining a first relationship function describing a substantially linear relationship between the first values of the stack difference parameter and the difference of the first values of the target parameter and the second values of the target parameter and a second relationship function describing a substantially linear relationship between the second values of the stack difference parameter and the difference of the first values of the target parameter and the second values of the target parameter.

18. The method of any of clauses 15-17, wherein determining the relationship function comprises making a 3-dimensional plot of the difference of the first values of the target parameter and the second values of the target parameter against the first values of the stack difference parameter and against the second values of the stack difference parameter.

19. The method of clause 18, wherein data points on the 3-dimensional plot substantially correlate to define an essentially flat plane and wherein a first relationship function is described by a slope of the plane relative to an axis of the first values of the stack difference parameter and a second relationship function is described by a slope of the plane relative to an axis of the second values of the stack difference parameter.

20. The method of clause 15 or clause 16, wherein determining the relationship function comprises determining a relationship function which describes a substantially linear relationship between: the difference of the first values of target parameter and the second values of target parameter; and the difference of the first values of stack difference parameter and the second values of stack difference parameter.

21. The method of clause 20, wherein determining the relationship function comprises making a plot of the difference of the first values of target parameter and the second values of target parameter against the difference of the first values of stack difference parameter and the second values of stack difference parameter, the relationship function being described by the slope of a line fitted to the plot.

22. The method of any of clauses 15-21, comprising determining a degree of correlation of 1) the first and/or second values of stack difference parameter, and 2) the difference of the first values of target parameter and the second values of target parameter.

23. The method of clause 22, wherein a degree of correlation is used in determining a measure of the accuracy of the determined part of a target parameter value which is independent of the un-designed difference in physical configuration.

24. The method of clause 22 or clause 23, comprising an initial optimization to determine a desired target from a plurality of candidate targets, the initial optimization comprising: obtaining plural sets of values comprising the first and second values of stack difference parameter and the first and second values of target parameter, for multiple samples of a plurality of candidate targets and a plurality of candidate measurement radiation pairs of the first measurement radiation and the second measurement radiation, each set of values relating to a different combination of one of the candidate targets and one of the candidate measurement radiation pairs; determining a degree of correlation for each of the plural sets of values; and selecting a desired target from one of the candidate targets based upon the determined degree of correlation for each set of values.

25. The method of clause 24, wherein selecting a desired target comprises: determining for each candidate target, the number of sets of values relating to that candidate target for which the determined degree of correlation is above a threshold; and selecting as the desired target, the candidate target for which the number of sets of values having a determined degree of correlation above a threshold is greatest.

26. The method of clause 24, wherein selecting a desired target comprises: determining for each candidate target, an average for the determined degree of correlation for each set of values relating to that candidate target; and selecting as the desired target, the candidate target for which the determined average is greatest.

27. The method of clause 24, wherein selecting a desired target comprises selecting a desired combination of one of the candidate targets and one of the candidate measurement radiation pairs based upon the determined degree of correlation for each set of values.

28. The method of clause 27, wherein selecting the desired combination comprises selecting the combination corresponding to the set of values for which the determined degree of correlation is highest.

29. The method of clause 27, wherein selecting the desired combination comprises selecting a subset of combinations, each of the subset of combinations corresponding to a set of values for which the determined degree of correlation is high.

30. The method of clause 29, wherein the subset of combinations comprises all combinations corresponding to a set of values for which the determined degree of correlation is above a threshold.

31. The method of clause 29 or clause 30, comprising selecting as the desired combination from the subset of combinations, a combination for which the corresponding set of values defines an essentially flat plane on a corresponding plot of the difference of the first values of target parameter and the second values of target parameter against the first values of stack difference parameter and against the second values of stack difference parameter.

32. The method of clause 30, wherein the desired combination is that for which the corresponding set of values best defines an essentially flat plane on the plot.

33. The method of clause 31, wherein, where there is more than one combination for which the corresponding set of values defines an essentially flat plane on the plot to an acceptable degree, the method further comprises: determining a degree of uncertainty for each of these set of values which define an essentially flat plane; and selecting as the desired combination, the combination for which the corresponding set of values has the smallest determined degree of uncertainty.

34. The method of clause 33, wherein the determined degree of uncertainty comprises a degree of uncertainty in the first and second values of target parameter.

35. The method of any of clauses 31-34, wherein the desired combination is selected as that which best reduces interdependency between the first values of target parameter and the second values of target parameter.

36. The method of any of clauses 27-35, comprising selecting either the first measurement radiation or the second measurement radiation of the measurement radiation pair of the desired combination as a desired measurement radiation based on which one results in the smallest value for measurement of the stack difference parameter.

37. The method of any of clauses 15-36, wherein the target parameter is overlay and the part of overlay value which is independent of the un-designed difference in physical configuration comprises a contribution due to a known imposed bias and a contribution due to an overlay error.

38. The method of any of clauses 15-36, wherein the target parameter is measurement beam intensity asymmetry.

39. The method of any of clauses 15-38, wherein the first measurement radiation has a selected characteristic which is different to that of the second measurement radiation, the selected characteristic of the measurement radiation comprising wavelength or polarization.

40. The method of any of clauses 15-39, comprising: measuring the adjacent periodic structures or targets using the first measurement radiation to obtain the first values of stack difference parameter; measuring the adjacent periodic structures or targets using the second measurement radiation to obtain the second values of stack difference parameter; measuring the target of the adjacent periodic structures or the targets of the plurality of adjacent targets using the first measurement radiation to obtain the first values of target parameter; and measuring the target of the adjacent periodic structures or the targets of the plurality of adjacent targets using the second measurement radiation to obtain the second values of target parameter.

41. The method of clause 40, wherein the measuring comprises: illuminating the adjacent periodic structures or targets with the measurement radiation and detecting the measurement radiation scattered by each periodic structure or target; and measuring intensity asymmetry in corresponding higher orders of the scattered measurement radiation.

42. The method of clause 39 or clause 40, wherein the measuring of the adjacent periodic structures or targets is performed prior to formation of a structure overlying the adjacent periodic structures or targets.

43. A method of selecting a target from a plurality of candidate targets, the method comprising: obtaining plural sets of values for a plurality of candidate measurement radiation pairs and a plurality of candidate targets, each candidate target comprising a first periodic structure horizontally adjacent to a second periodic structure, each set of values relating to a different combination of one of the candidate targets and one of the candidate measurement radiation pairs, each set of values comprising, for multiple samples of the candidate target: first values of stack difference parameter and second values of stack difference parameter of the adjacent periodic structures of the candidate target using, respectively, a first measurement radiation and a second measurement radiation of the candidate measurement radiation pair, the stack difference parameter representing an un-designed difference in physical configuration between adjacent periodic structures of a target, and first values of target parameter and second values of target parameter of the candidate target using, respectively, the first measurement radiation and the second measurement radiation; for each set of values, determining a degree of correlation between the first and/or second values of stack difference parameter and the difference of the first values of target parameter and the second values of target parameter; and selecting a desired target from one of the candidate targets based upon the determined degree of correlation for each set of values.

44. The method of clause 43, wherein selecting a desired target comprises: determining for each candidate target, the number of sets of values relating to that candidate target for which the determined degree of correlation is above a threshold; and selecting as the desired target, the candidate target for which the number of sets of values having a determined degree of correlation above a threshold is greatest.

45. The method of clause 43, wherein selecting a desired target comprises: determining for each candidate target, an average for the determined degree of correlation for each set of values relating to that candidate target; and selecting as the desired target, the candidate target for which the determined average is greatest.

46. The method of clause 43, wherein selecting a desired target comprises selecting a desired combination of one of the candidate targets and one of the candidate measurement radiation pairs based upon the determined degree of correlation for each set of values.

47. The method of clause 46, wherein selecting a desired combination comprises selecting the combination corresponding to the set of values for which the determined degree of correlation is highest.

48. The method of clause 46, wherein selecting a desired combination comprises selecting a subset of combinations, each of the subset of combinations corresponding to a set of values for which the determined degree of correlation is high.

49. The method of clause 48, wherein the subset of combinations comprises all combinations corresponding to a set of values for which the determined degree of correlation is above a threshold.

50. The method of clause 48 or clause 49, comprising selecting as the desired combination from the subset of combinations, a combination for which the corresponding set of values defines an essentially flat plane on a corresponding plot of the difference of the first values of target parameter and the second values of target parameter against the first values of stack difference parameter and against the second values of stack difference parameter.

51. The method of clause 50, wherein the desired combination is that for which the corresponding set of values best defines a flat plane on the plot.

52. The method of clause 50, wherein, where there is more than one combination for which the corresponding set of values defines an essentially flat plane on the plot to an acceptable degree, the method further comprises: determining a degree of uncertainty for each of these set of values which define an essentially flat plane; and selecting as the desired combination, the combination for which the corresponding set of values has the smallest determined degree of uncertainty.

53. The method of clause 52, wherein the determined degree of uncertainty comprises a degree of uncertainty in the first and second values of target parameter.

54. The method of any of clauses 50-53, wherein the desired combination is selected as that which best reduces interdependency between the first values of target parameter and the second values of target parameter.

55. The method of any of clauses 46-54, comprising selecting either of the first measurement radiation or the second measurement radiation of the measurement radiation pair of the desired combination as a desired measurement radiation based on which one results in the smallest value for measurement of stack difference parameter.

56. The method of clause 55, comprising performing an overlay measurement using the desired measurement radiation on the desired target of the desired combination.

57. The method of any of clauses 46-54, comprising performing an overlay measurement using the measurement radiation pair of the desired combination on the desired target of the desired combination.

58. The method of any of clauses 46-57, comprising performing an overlay measurement on the desired target.

59. The method of any of clauses 46-58, wherein the target parameter is overlay and the part of overlay value which is independent of the un-designed difference in physical configuration comprises a contribution due to a known imposed bias and a contribution due to an overlay error.

60. The method of any of clauses 46-58, wherein the target parameter is measurement beam intensity asymmetry.

61. A metrology apparatus for measuring a parameter of a lithographic process, the metrology apparatus being operable to perform the method of any of clauses 1-60.

62. A non-transitory computer program product comprising machine-readable instructions for causing a processor to cause performance of the method of any of clauses 1-60.

63. A system comprising: an inspection apparatus configured to provide a beam of radiation on two adjacent periodic structures or measurement targets on a substrate and to detect radiation diffracted by the targets to determine a parameter of a patterning process; and the non-transitory computer program product of clause 62.

64. The system of clause 63, further comprising a lithographic apparatus comprising a support structure configured to hold a patterning device to modulate a radiation beam and a projection optical system arranged to project the modulated radiation beam onto a radiation-sensitive substrate.

Although specific reference may have been made above to the use of embodiments in the context of optical lithography, it will be appreciated that embodiments of the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of selecting a metrology target from a plurality of candidate metrology targets, the method comprising:
obtaining plural sets of values for a plurality of candidate measurement radiation pairs and a plurality of candidate metrology targets, each candidate metrology target comprising a first periodic structure horizontally adjacent to a second periodic structure, each set of values relating to a different combination of one of the candidate metrology targets and one of the candidate measurement radiation pairs, each set of values comprising, for multiple samples of the candidate metrology target:
first values of stack difference parameter and second values of stack difference parameter of the adjacent periodic structures of the candidate metrology target using, respectively, a first measurement radiation and a second measurement radiation of the candidate measurement radiation pair, the stack difference parameter representing an un-designed difference in physical configuration between adjacent periodic structures of a metrology target, and
first values of metrology target parameter and second values of metrology target parameter of the candidate metrology target using, respectively, the first measurement radiation and the second measurement radiation;
for each set of values, determining a degree of correlation between the first and/or second values of stack difference parameter and the difference of the first values of metrology target parameter and the second values of metrology target parameter; and
selecting a desired metrology target from one of the candidate metrology targets based upon the determined degree of correlation for each set of values.

2. The method of claim 1, wherein selecting a desired metrology target comprises:
determining for each candidate metrology target, the number of sets of values relating to that candidate metrology target for which the determined degree of correlation is above a threshold; and
selecting as the desired metrology target, the candidate metrology target for which the number of sets of values having a determined degree of correlation above a threshold is greatest.

3. The method of claim 1, wherein selecting a desired metrology target comprises:
determining for each candidate metrology target, an average for the determined degree of correlation for each set of values relating to that candidate metrology target; and
selecting as the desired metrology target, the candidate metrology target for which the determined average is greatest.

4. The method of claim 1, wherein selecting a desired metrology target comprises selecting a desired combination of one of the candidate metrology targets and one of the candidate measurement radiation pairs based upon the determined degree of correlation for each set of values.

5. The method of claim 4, wherein selecting a desired combination comprises selecting the combination corresponding to the set of values for which the determined degree of correlation is highest.

6. The method of claim 4, wherein selecting a desired combination comprises selecting a subset of combinations, each of the subset of combinations corresponding to a set of values for which the determined degree of correlation is high.

7. The method of claim 6, wherein the subset of combinations comprises all combinations corresponding to a set of values for which the determined degree of correlation is above a threshold.

8. The method of claim 6, comprising selecting as the desired combination from the subset of combinations, a combination for which the corresponding set of values defines an essentially flat plane on a corresponding plot of the difference of the first values of metrology target parameter and the second values of metrology target parameter against the first values of stack difference parameter and against the second values of stack difference parameter.

9. The method of claim 8, wherein the desired combination is that for which the corresponding set of values best defines a flat plane on the plot.

10. The method of claim 8, wherein, where there is more than one combination for which the corresponding set of values defines an essentially flat plane on the plot to an acceptable degree, the method further comprises:
determining a degree of uncertainty for each of these set of values which define an essentially flat plane; and
selecting as the desired combination, the combination for which the corresponding set of values has the smallest determined degree of uncertainty.

11. The method of claim 10, wherein the determined degree of uncertainty comprises a degree of uncertainty in the first and second values of metrology target parameter.

12. The method of claim 8, wherein the desired combination is selected as that which best reduces inter-dependency between the first values of metrology target parameter and the second values of metrology target parameter.

13. The method of claim 4, comprising selecting either of the first measurement radiation or the second measurement radiation of the measurement radiation pair of the desired combination as a desired measurement radiation based on which one results in the smallest value for measurement of stack difference parameter.

14. The method of claim 13, comprising performing an overlay measurement using the desired measurement radiation on the desired metrology target of the desired combination.

15. The method of claim 4, comprising performing an overlay measurement using the measurement radiation pair of the desired combination on the desired metrology target of the desired combination.

16. The method of claim 4, comprising performing an overlay measurement on the desired metrology target.

17. The method of claim 4, wherein the metrology target parameter is overlay and the part of overlay value which is independent of the un-designed difference in physical configuration comprises a contribution due to a known imposed bias and a contribution due to an overlay error.

18. The method of claim 4, wherein the metrology target parameter is measurement beam intensity asymmetry.

19. A non-transitory computer program product comprising machine-readable instructions therein that, when executed by a processor system, are configured to cause the processor system to at least:
obtain plural sets of values for a plurality of candidate measurement radiation pairs and a plurality of candidate metrology targets, each candidate metrology target comprising a first periodic structure horizontally adjacent to a second periodic structure, each set of values relating to a different combination of one of the candidate metrology targets and one of the candidate measurement radiation pairs, each set of values comprising, for multiple samples of the candidate metrology target:
first values of stack difference parameter and second values of stack difference parameter of the adjacent periodic structures of the candidate metrology target using, respectively, a first measurement radiation and a second measurement radiation of the candidate measurement radiation pair, the stack difference parameter representing an un-designed difference in physical configuration between adjacent periodic structures of a metrology target, and
first values of metrology target parameter and second values of metrology target parameter of the candidate metrology target using, respectively, the first measurement radiation and the second measurement radiation;
for each set of values, determine a degree of correlation between the first and/or second values of stack difference parameter and the difference of the first values of metrology target parameter and the second values of metrology target parameter; and
select a desired metrology target from one of the candidate metrology targets based upon the determined degree of correlation for each set of values.

20. A metrology system comprising:
an optical system configured to provide a beam of radiation onto a substrate;
a detector system configured to detect radiation redirected from the substrate to determine a parameter related to the substrate; and
the non-transitory computer program product of claim 19.

21. A system comprising:
an inspection apparatus configured to provide a beam of radiation on two adjacent periodic structures or measurement targets on a substrate and to detect radiation diffracted by the targets to determine a parameter of a patterning process; and
the non-transitory computer program product of claim 19.

* * * * *